US012778790B2

(12) United States Patent
Gomez et al.

(10) Patent No.: US 12,778,790 B2
(45) Date of Patent: Nov. 3, 2026

(54) ERGONOMIC URINE COLLECTOR

(71) Applicants: Teresa Acevedo Gomez, Burnaby (CA); Arnulfo Galan Cadena, Burnaby (CA)

(72) Inventors: Teresa Acevedo Gomez, Burnaby (CA); Arnulfo Galan Cadena, Burnaby (CA)

(73) Assignee: Teresa Acevedo Gomez, Burnaby (CA)

( * ) Notice: Subject to any disclaimer, the term of this patent is extended or adjusted under 35 U.S.C. 154(b) by 208 days.

(21) Appl. No.: 18/394,180

(22) Filed: Dec. 22, 2023

(65) Prior Publication Data

US 2024/0238114 A1 Jul. 18, 2024

Related U.S. Application Data

(60) Provisional application No. 63/479,996, filed on Jan. 14, 2023.

(51) Int. Cl.
*A47K 11/12* (2006.01)
*A61F 5/455* (2006.01)
*A61G 9/00* (2006.01)

(52) U.S. Cl.
CPC ............ *A61F 5/4556* (2013.01); *A47K 11/12* (2013.01); *A61G 9/006* (2013.01)

(58) Field of Classification Search
CPC ........................ A47K 11/02–023; A47K 11/06; A47K 11/12; A61B 10/007; A61F 5/44;
(Continued)

(56) References Cited

U.S. PATENT DOCUMENTS 1,928,170 A * 9/1933 Dwork .................... A61F 5/455 4/144.4
3,131,403 A * 5/1964 Hill .......................... A61F 5/455 D24/118

(Continued)

FOREIGN PATENT DOCUMENTS

DE 29609181 * 8/1996 ............. A47K 11/12
WO WO2021191640 * 9/2021 ........... A47K 11/026

OTHER PUBLICATIONS

Communication issued by Canadian Intellectual Property Office on Jul. 2, 2025.

*Primary Examiner* — David P Angwin
*Assistant Examiner* — Nicholas A Ros

(57) ABSTRACT

Examples of a disposable female urine collection system are described. The urine collection system comprises a receiving funnel with an upper rim defining an entrance opening and a receiving body extending downwardly from the entrance opening. A handle integrated with the receiving funnel is provided to help positioning and holding firmly the urine collection system during use. A removable lid is sized to close the entrance opening of the receiving funnel and a tube spout is integrally connected to the lower part of the funnel. A collection container with a collection cavity and an opening mouth is connected to the tube spout. The urine collection systems can be used in public washrooms to prevent user being exposed to pathogen microorganism, users that are in laying and/or seated/half-seated and bed-ridden position to avoid direct contact with public bed pan seats, or as urine samples collectors for medical analysis.

14 Claims, 22 Drawing Sheets

(58) Field of Classification Search

CPC ........... A61F 5/453–455; A61F 5/4556; A61G 9/00–006

See application file for complete search history.

(56) References Cited

U.S. PATENT DOCUMENTS

| | | | | | |
|---|---|---|---|---|---|
| 3,163,869 | A * | 1/1965 | Johnson | A61G 9/006 | 4/144.1 |
| 4,164,795 | A * | 8/1979 | Johnson | A61G 9/006 | 4/144.1 |
| 4,568,339 | A * | 2/1986 | Steer | A61F 5/455 | 4/144.3 |
| 5,415,475 | A * | 5/1995 | Sandy | A61J 19/00 | 383/77 |
| 5,797,147 | A * | 8/1998 | Young | A61G 9/006 | 604/350 |
| 5,920,916 | A * | 7/1999 | Norton | A61B 10/007 | 4/144.3 |
| 6,684,414 | B1 | 2/2004 | Rehrig | | |
| 9,539,158 | B2 * | 1/2017 | Cassidy | A61G 9/006 | |
| 11,931,014 | B2 | 3/2024 | Pryor | | |
| 2002/0193762 | A1 * | 12/2002 | Suydam | A61G 9/006 | 604/327 |
| 2005/0070864 | A1 * | 3/2005 | Fellion | A61F 5/4556 | 604/346 |
| 2007/0010792 | A1 * | 1/2007 | Kimura | A61F 5/4556 | 604/329 |
| 2010/0094233 | A1 * | 4/2010 | Ashworth | A61F 5/4556 | 604/317 |
| 2018/0177247 | A1 * | 6/2018 | Lin | A61F 5/4556 | |
| 2020/0121300 | A1 * | 4/2020 | Moore | B67C 11/00 | |
| 2021/0007719 | A1 | 1/2021 | Pryor | | |

* cited by examiner (A) (B) (C)

ERGONOMIC URINE COLLECTOR

CROSS REFERENCE TO RELATED APPLICATIONS

This application claims priority of U.S. Provisional Patent Application No. 63/479,996 filed Jan. 14, 2023, which is incorporated herein by reference.

FIELD

This invention generally relates to a urine collector and more particularly to a urine collector that is ergonomic and can be positioned and held in place during urine collection.

BACKGROUND

Generally, when outside their home and in need of urination, women use unsanitary public toilets and risk sitting on a toilet seat that may be contaminated with germs, bacteria, fungi, and viruses. Thus, using unsanitary places and sharing the same public toilet seat increases the chances of potentially harmful germs and urinary tract infections. To avoid the risk, females try hover and squat positions when using unsanitary places and public toilets to avoid contact with the unsanitary surfaces, an action which is uncomfortable and cumbersome.

Public washrooms and their use have a big environmental impact associated with big water waste and paper waste. Traditional urinal system, such as flushed toilets, consume huge amounts of water. Typically, busy commercial spaces can account for as much as 50% of total water consumption in a bigger cites.

To solve the above-mentioned problems, waterless urinals are added to the public washrooms that can be used without the need of a user to touch any surface of the toilet and are usually consuming no water or very small amount of water, as such urinals do not flush. However, such urinals can be used only by male population. Due to the male anatomy, they can discharge the urine in a horizontal manner with comfort, cleanliness and convenience; however women cannot use such urinals. Female urethra is located beneath the labia minora and labia majora midway up the vagina, such that the urine flows vertically downward by gravity. Also, based on the configuration of the female's genitalia, the urine flows turbulently outwardly in random direction(s) in which the fluid continuously undergoes irregular fluctuations.

Most of the known solutions for urine collection designed for females try to simulate natural urination process of the male. For example, female urine that carries out from the urethra flowing downward is caught by a female urinal device that has a funnel which changes the direction of travel from vertical to horizontal in order to reach the urinal. Using such known urine collectors, there is a risk of leak due to the turbulent flow of the urine and spill out over the clothing.

Therefore, an improved system and method for urine collection that may solve the above-mentioned problems are needed.

SUMMARY

In one aspect, a urine collection system is provided. The urine collection system comprises a receiving funnel that has an entrance opening formed at an upper part of the receiving funnel, an exit opening formed at a lower part of the receiving funnel and a body extending between the entrance opening and the exit opening. The body is designed to extend downwardly from the entrance opening and has a diameter at the entrance opening that is bigger than a diameter of the body at the exit opening. The receiving funnel and the entrance opening are sized and shaped to fit around user genitalia parts surrounding a perimetral region of all the genitalia parts. A handle is connected to the receiving funnel to help positioning and holding firmly the urine collection system against a user body during use. The urine collection system further comprises a collection container that has a body with a collection cavity and an opening mouth connected to the lower part of the receiving funnel.

In another aspect, the handle comprises a hole shaped such that at least one finger is insertable through the hole. The hole is shaped as a single-finger hole, a double-fingers hole or a three-fingers hole.

In one aspect, the body of the receiving funnel has a straight conical wall, a concave rounded inwardly wall or a convex rounded outwardly wall.

In one aspect, the collection container comprises a closure formed down from and in proximity to the opening mouth. The closure is configured to close the collection container. The closure comprises an interlocking mechanism to tightly close the collection container.

In another aspect, the body of the receiving funnel has a curved shape with the upper part extending away from the entrance opening and forming an upper funnel chamber and a curving funnel part. The receiving funnel further comprises an extending lever extending of the entrance opening towards a posterior end of the funnel's upper part. The extending lever has a peripheral edge that forms a support surface to support the receiving funnel on a surface. A deflecting barrier is also provided that extends away from an inner surface of the upper part into an interior of the funnel body.

In one aspect, the collection container and the receiving funnel are sealed tightly forming a spout pouch. The receiving funnel comprises a removable lid designed and sized to close the entrance opening of the receiving funnel and a tube spout integrally connected to the lower part of the receiving funnel. The tube spout has a body defining a passageway with an upper opening joined to the exit opening of the receiving funnel and a lower opening. The opening of the collecting container is tightly sealed to at least portion of the tube spout such that the lower opening of the tube spout is within the inner cavity of the collection container.

In another aspect, the upper part and the lower part of the receiving funnel are detachably connected. The upper part of the receiving funnel comprises a ledge that extends inwardly of the lower edge of the upper part and the lower part of the receiving funnel comprises a flange that extends outwardly from an upper edge of the lower part of the receiving funnel. When the upper part and the lower part are in an attached position the flange rests on the ledge and the funnel body of the lower part extends downwardly from the lower edge of the upper part.

In one aspect, the urine collection system is used as a medical urine samples collection container. The receiving funnel is detachable and removed from the collection container. The collection container is tightly closed using a closure.

In addition to the aspects and embodiments described above, further aspects and embodiments will become apparent by reference to the drawings and study of the following detailed description.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure. Sizes and relative positions of elements in the drawings are not necessarily drawn to scale. For example, the shapes of various elements and angles are not drawn to scale, and some of these elements are arbitrarily enlarged and positioned to improve drawing legibility.

FIG. 26 (A) shows the use of female urinal collection system when the user is in a standing position; FIG. 26(B) shows the use of female urinal collection system when the user is in a lay-down position.

DETAILED DESCRIPTION

Embodiments of this invention provide a urinal collection system that is configured to be used by the user. The urinal collection system can be used by users with female anatomy genital parts and can comprise a collecting container to contain urine ejected by the user and an ergonomically shaped receiving funnel or spout with an entrance opening and a handle to position the entrance opening against the user's genital parts while keeping user's hand away from the collection system.

Figure 1A:
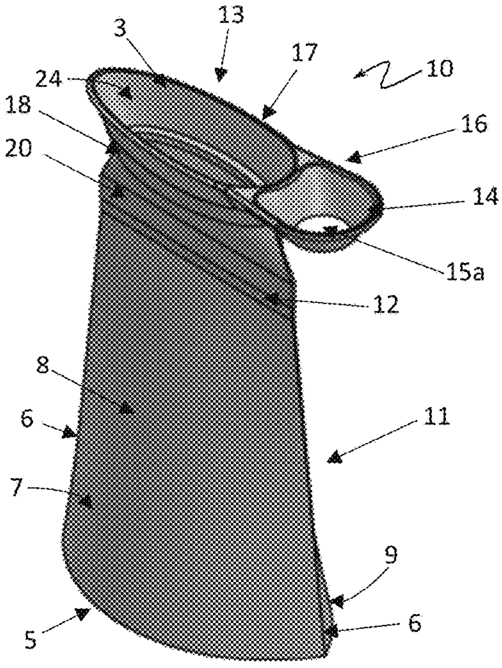
FIG. 1A is a perspective view of an example of a female urine collection system according to an embodiment of the present invention with a handle with a single finger opening.

FIG. 1A shows a perspective view of an example of a urinal collection system (10) of the present invention. The collection system (10) comprises a collection container or pouch (11) and a receiving funnel (13) in communication with the collection container (11). The collection container (11) can be a bag/pouch or any other suitable vessel coupled to the funnel (13) and configured to collect the urine and at least temporarily store such collected urine. In some embodiments, the collection container (11) can be designed as pouch with a flexible body that can fold when not in use and unfold when urine is collected during use. The collection container can have various different sizes and shapes without departing from the scope of the invention.

In the illustrated example embodiment, the collection container (11) can have a base (21) and a side wall (8) extending upward from the base (21) creating an inner cavity configured to receive and contain the urine collected during use. An opening is formed at a top edge (20) of the collection container (11) to provide access to the inner cavity of the collection container (11). In the embodiment illustrated in FIGS. 1-6, the side wall (8) comprises a first side wall (7) and the second side wall (9) joined together along the two side seams (6) and joined with the base (21) along a lower edge (5). The base (21) may have a crease (22) that allows the collection container (11) to be foldable and collapsible when empty. The collection container (11) shown in FIGS. 1-6 can be a bag with a pyramidical shape however this is only exemplary and persons skilled in the art would understand that the collection container (11) can be any other container configured to hold liquid fluids.

In one embodiment, the collection system (10) can further comprise a closure (12) configured to close and/or open the opening of the collection container (11). The closure (12) can be formed underneath the top edge (20) of the collection container (11) and can be configures to tightly seal the collection container (11) when in closed position.

The collection container (11) can be made of a waterproof material that can prevent the fluid penetrating and leaking through the collection container (11). For example, the collection container can be made from synthetic polymer (i.e., polyvinyl chloride (PVC), Polyester, Polypropylene), a biodegradable polymer, a biopolymer, an aluminum foil, a paper or a fabric/textile with a waterproof inner wall or waterproof coating configured as liquid fluid barrier, or any other flexible or pliable material configured to contain liquid fluids without liquid fluid penetrating through the wall of the container. In addition, the collection container (11) can be made of any other material such as natural or synthetic rubber, ceramic, plastic or metal. In some implementation, the collection container (11) ca be made of a flexible material that will allow the collection container (11) to be easily fold or roll to a smaller size for storing purposes. In some implementations, the collection container can comprise sheets of same or different materials laminated together.

The receiving funnel (13) can comprise an upper part (2) with a ring-shaped body (3) having an upper rim (17) defining an entrance opening (24) and a side wall extending downwardly from the upper rim (17). A lower part (4) of the receiving funnel (13) is a funnel body (26) extending downwardly from the upper part and forms a funnel conduit to direct the urine through the receiving funnel (13) into the collection container (11). A diameter (D1) of the body (26) at the entrance opening (24) is bigger than a diameter (D2) of the body (26) at its lower, bottom edge where an exit opening (18) is formed. The receiving funnel (13) and the entrance opening (24) can be sized and shaped to fit around female genitalia parts surrounding a perimetral region of all female genitalia parts. A handle (14) that can be provided to help positioning and holding firmly the urine collection system (10) during use.

The receiving funnel (13) can have various sizes and shapes and can be made of any suitable material. In one embodiment the receiving funnel (13) can be made by molding using the wet pressing process, however any other suitable manufacturing process can be used without departing from the scope of the invention. For example, the receiving funnel can be made by 3D printing, molding, injection molding or any other suitable technique or process. Any suitable materials can be used for making the receiving funnel (13), such as for examples, plastic material made of synthetic or bio polymers, rubber, glass, metal or any other suitable material. In some implementations, the receiving funnel can be made from 100% biodegradable and compostable materials, such us sugar cane fibers, bamboo fibers, sorghum, wheat straw and others. The receiving funnel (13) can also have a smooth surface and can have variety of finishes to enhance user experience during use. In some embodiments, the receiving funnel (13) can be made of flexible material with good nesting and stacking capabilities for packaging purposes.

The receiving funnel (13) shown in exemplary embodiment in FIGS. 1-6, has a conical shape (see FIGS. 5 and 6) with the ring-shaped body (3) and the funnel body (26) having straight walls and elliptical entrance opening (24) creating funnel which gradually narrows from the flat-profile elliptical upper rim (17) forming the elliptical opening (24) towards its lower part and exit opening (18). The lower part of the funnel is open (at the exit opening (18)) and is in communication with the cavity of the collection container (11), when the closure (12) is in an open position. The collection container (11) is connected to the receiving funnel (13) along a transition portion (19). The transition portion (19) can be integrated to the top edge/mouth (20) of the collection container (11) that encloses the bottom edge of the lower part (4) of the receiving funnel (13) such that no liquid fluid is spilled out when exiting the funnel and entering the collection container (11). In some embodiments, the transition portion (19) can be part of the receiving funnel (13) such as for example, it can be connected to the lower part (4) integrated with the funnel body (26). In one embodiment, the receiving funnel (13) is permanently connected to the collection container (11) such that the collection container (11) is integrated and continuous with the receiving funnel (13) forming the urine collection system (10). For example, the receiving funnel (13) and the collection container (11) can be manufactured as a single integrated structure using a molding (e.g., an injection molding) process or an additive manufacturing (3D-printing) process or any other suitable process. In some implementations, the receiving funnel (13) and the collection container (11) can be thermally bonded or glued at the transitioned portion (19) or can be mechanically connected using any suitable fasteners such as clamps, screws, nuts, bolts, washers, rivets, nails etc.

In another embodiment, the collection container (11) can be detachable from the receiving funnel (13), such that the funnel (13) and the collection container (11) are reversibly attached, using for example loops, zippers, snaps, buttons, hooks or any other male and female element that are locked together. For example, a two-part connector (not shown) can be positioned at the transitioned portion (19) such that the collection container (11) can be attached to the receiving funnel (13), in a detachable manner, when the urine collection system (10) is in use and can be detached and stored when the collection system is not in use. For example, the two-part connector can be a zipper seal (i.e., a single or double zipper seal) to tightly secure the collection container (11) to the receiving funnel (13). The two-part connector can be any other suitable connector, such as for example, a snap type of connector, hook and loops, Velcro™ connector or any other known and suitable connector. In yet another embodiment, the receiving funnel (13) can be separate and independent from the collectable container. For example, the collection container can be a bedpan or urinal that can be used for bedridden users. In such embodiments, the exit opening (18) of the receiving funnel (13) can be positioned in proximity to and in communication with the collecting container cavity without being joined to the collecting container.

In some implementations, the urine collection system (10) can be reusable. For example, the urine collection system (10) can be washable and usable multiple times. For example, during long backcountry hiking trips, the system (10) can be cleaned and reused. In other implementations, the urine collection system (10) can be disposable after use. The urine collection system (10) can be made of biodegradable material to prevent long lasting environmental harm. In yet another implementation, one part of the urine collection system (10) can be reusable while one part can be disposable. For example, the receiving funnel (13) of the urine collection system (10) can be reusable while the collection container (11) can be disposable and vice versa, the receiving funnel (13) of the urine collection system (10) can be disposable while the collection container (11) can be reusable.

Figure 25:
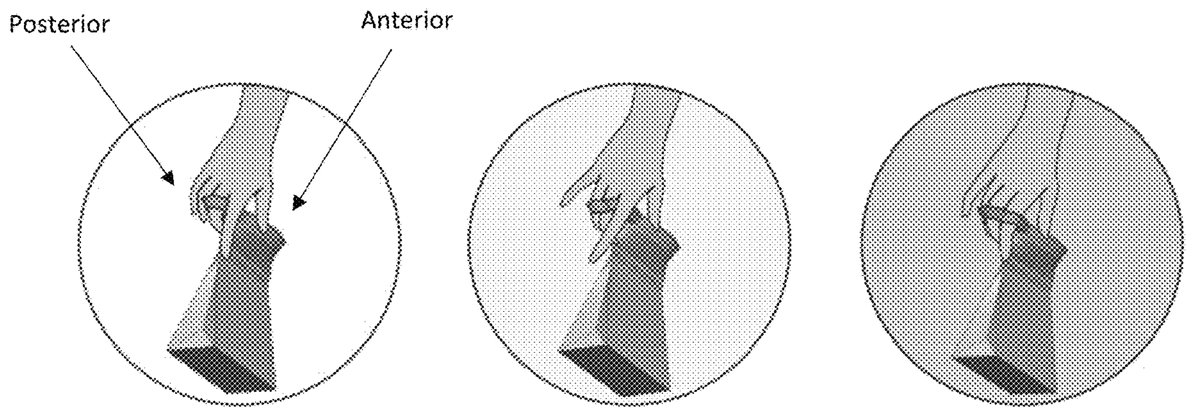
FIG. 25 is a perspective view of a female urinal collection system with handle comprising: (A) a single-finger hole, (B) a double-fingers hole; and (C) three-fingers hole, showing user holding the system when in use.

The handle (14) can be attached to the body (26) of the receiving funnel (13). In some implementations, the handle (14) can be integrated with the receiving funnel (13), such as for example it can be molded, or 3D printed as integral part of the receiving funnel (13). However, persons skilled in the art would understand that the handle (14) can be attached permanently or detachably to the receiving funnel (13) without departing from the scope of the invention. For example, the handle (14) can be attached to the funnel body using any suitable mechanical fastener such as screws, nuts, bolts, washers, anchors, rivets, nails, clamps or it can be glued or bonded to the body (26) of the receiving funnel (13). In one embodiment, the handle (14) of the urine collection system (10) can comprise at least one hole (15*a*) shaped such that at least one finger is insertable through the hole (15*a*). The handle (14) can be secured to the receiving funnel (13) and can have ergonomic shape that allows the user to grip the funnel (13) firmly at an anterior end (16) only, away from the receiving funnel entrance opening (24) while still be able to apply pressure (if necessary) to the anterior portion of the vagina, around the labia majore. In one embodiment, shown in FIGS. 1A, 2A and 3A, the hole (15*a*) in the handle (14) is shaped and designed as a single-finger hole (15*a*) such that only one finger can be insertable through the hole (15*a*). For example, during use only one finger is inserted through the hole (e.g., see FIG. 25A that shows a middle finger being inserted through the hole (15*a*) to firmly hold and press the collection system (10) against the user body. Any other finger (e.g., thumb, index or ring finger) can be inserted through the single-finger sized hole (15*a*) to firmly hold the collection system (10) during use without departing from the scope of the invention. In another embodiment, shown in FIGS. 1B, 2B, 3B, 7, 9, 10, 19A, 20A and 21A, the handle (14) has a hole (15*b*) that is shaped and designed as a double(two)-fingers hole such that two fingers can be insertable through the hole (15*b*) during use. For example, FIG. 25B shows the middle and ring fingers being inserted through the double-fingers sized hole (15*b*) to firmly hold and press the collection system (10) against the user body, however persons skilled in the art would understand that the user can insert any other two fingers without departing from the scope of the invention. In some implementations, the double-fingers hole (15*b*) can be designed as two separate holes, where each hole can be sized and shaped so that a single finger is insertable through each hole. In the embodiment shown in FIGS. 1C, 2C, 3C, 13, 17, 18 and 19C, the handle (14) has a hole (15*c*) that is sized and shaped as a three-fingers hole (15*c*) such that three fingers can be insertable through the hole (15*c*) during use. For example, FIG. 25C shows the index, middle and ring fingers being inserted through the three-fingers sized hole (15*c*) to firmly hold and press the collection system (10) against the user body, however persons skilled in the art would understand that the user can insert any other three fingers without departing from the scope of the invention. In some implementations, the three-fingers hole (15*c*) can be designed as three separate holes, such that each hole can be sized and shaped so that a single finger is insertable through each hole. In some implementations, the hole in the handle (14) can allow the user to attach the urine collection system (10) to backpacks, begs, belt loops, or any additional weight-bearing fabric, allowing for hands-free carry (e.g., to hands-free carrying the urine collection system during hiking or climbing activities).

The collection container (11) may or may not comprise a closure (12). In one embodiment the closure (12) is comprised of an interlocking mechanism to seal the collection container (11). In one embodiment, the interlocking mechanism comprises a male and female element that are manually and/or mechanistically locked together to create a seal. In another embodiment, the interlocking mechanism is comprised of one or several zipper sealed closures to ensure a leak proof seal. In some implementations of the urine collection system (10), the closure (12) can be omitted (e.g., in cases when a bedpan is a collection container), and the urine sample can be immediately disposed in for example a waterless urinals that may be available in public washrooms. The collection container (11) may be disposable or can be reusable.

In some embodiments, the urine collection system (10) can be used for medical urine samples collection. For example, the collection container (11) can be sized (for example, about 80-400 milliliters) to collect enough urine sample required for the medical analysis. In some embodiment, when the collection system is used as medical lab urine collection system, the collection container (11) can have 90 milliliters capacity, while in another embodiments it can have up to 350 milliliters volume capacity. In some embodiments, the collection container (11) of the medical lab urine collection system (10) can be labelled with the patient information and can be closed using the closure (12) and detached from the receiving funnel (13) so that only the container (11) containing the urine sample is left for analysis while the rest of the collection system (10) is disposed.

Figure 1B:
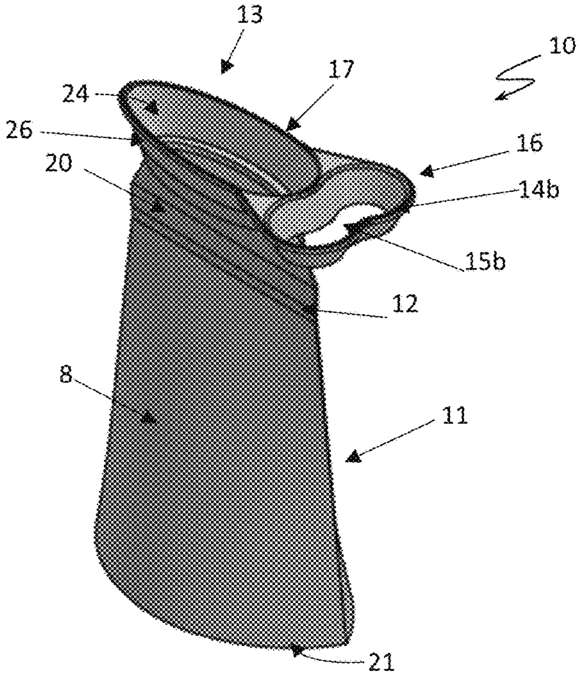
FIG. 1B is a perspective view of an example of a female urine collection system according to an embodiment of the present invention with a handle with a two-fingers opening.
Figure 1C:
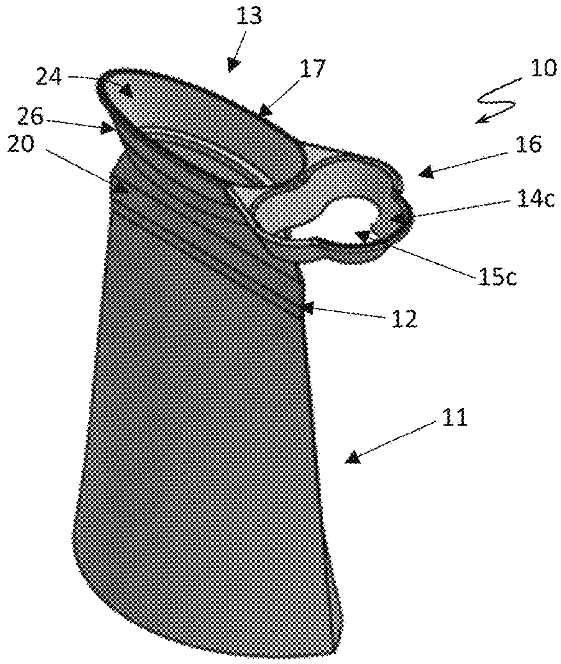
FIG. 1C is a perspective view of an example of a female urine collection system according to an embodiment of the present invention with a handle with a three-fingers opening.
Figure 2A:
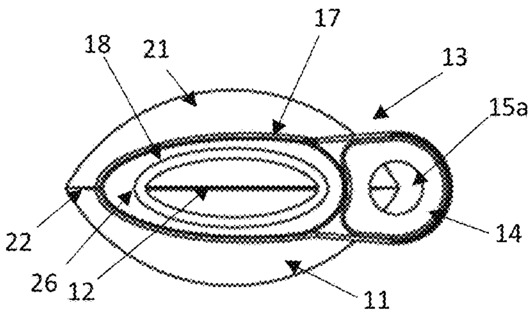
FIG. 2A is a top view of the embodiment shown in FIG. 1A.
Figure 2B:
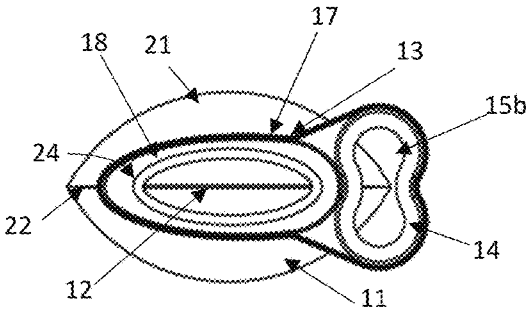
FIG. 2B is a top view of the embodiment shown in FIG. 1B.
Figure 2C:
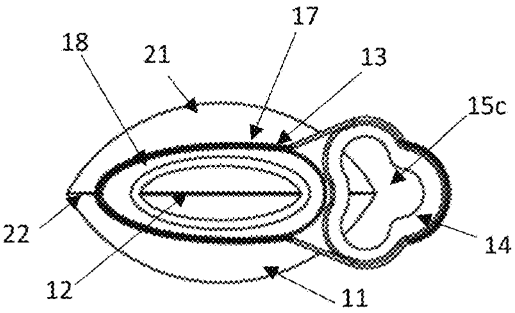
FIG. 2C is a top view of the embodiment shown in FIG. 1C.

FIGS. 2A-2C show a top view of the urinal system (10) described in respective FIGS. 1A-1C. As shown in FIG. 2 the receiving funnel (13) has an elliptical shape with wide elliptical upper rim (17) along the entrance opening (24) and body (26) that narrows towards the lower part and the exit opening (18). The exit opening (18) can have elliptical or circular shape or any other different form/shape without departing from the scope of the invention. In some implementations, the receiving funnel can have a circular shape with wide upper rim (17) along a circularly shaped entrance opening and body that narrows towards the lower exit opening (18) which can have a circular, elliptical or any other suitable shape. The ring-shape body (3) and the funnel body (26) narrows from the wider entrance opening (24) towards the lower exit opening (18), such that the exit opening is smaller than the entrance opening. The handle (14) shown in FIG. 2A has the one (single)-finger hole (15*a*) design for ergonomic grip while the embodiment shown in FIG. 2B illustrate the handle (14) with the double-finger hole (15*b*) design, and FIG. 2C shows an embodiment of the collection system (10) with the handle (14) with the three-finger hole (15*c*) design. The urinal collection system (10) shown in FIG. 2 illustrates the closure (12) in a closed position when in the collection container (11) is a sealed, as illustrated by the line (12) which represents the closure (12) in closed position.

Figure 3A:
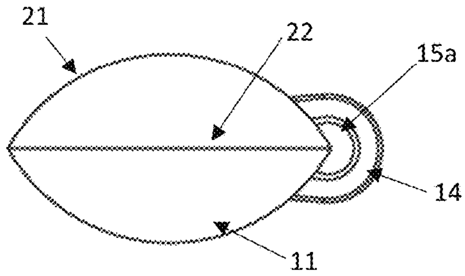
FIG. 3A is a bottom view of the embodiment shown in FIG. 1A.
Figure 3B:
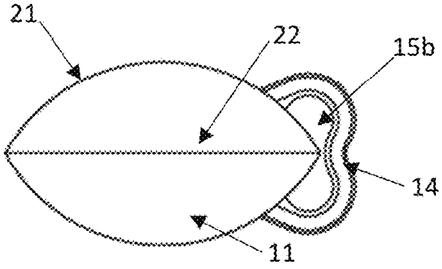
FIG. 3B is a bottom view of the embodiment shown in FIG. 1B.
Figure 3C:
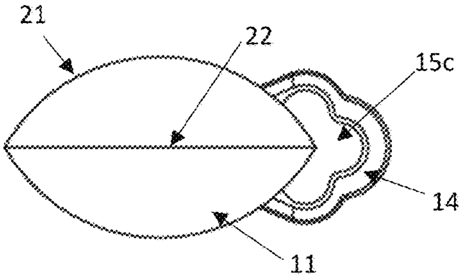
FIG. 3C is a bottom view of the embodiment shown in FIG. 1C.

FIGS. 3A-3B is a bottom view of the urinal collection system (10) described in respective FIGS. 1A-1C. The collection container (11) is shaped such that the circumference of the base is greater than the top opening where the conical funnel is attached. The collection container has a crease (22) which allows it to be foldable and collapsible when empty. FIG. 3A has the one (single)-finger hole (15*a*) design for ergonomic grip; FIG. 3B illustrate the handle (14) with the double-finger hole (15*b*) design, and FIG. 3C shows an embodiment of the collection system (10) with the handle (14) with the three-finger hole (15*c*) design.

Figure 4:
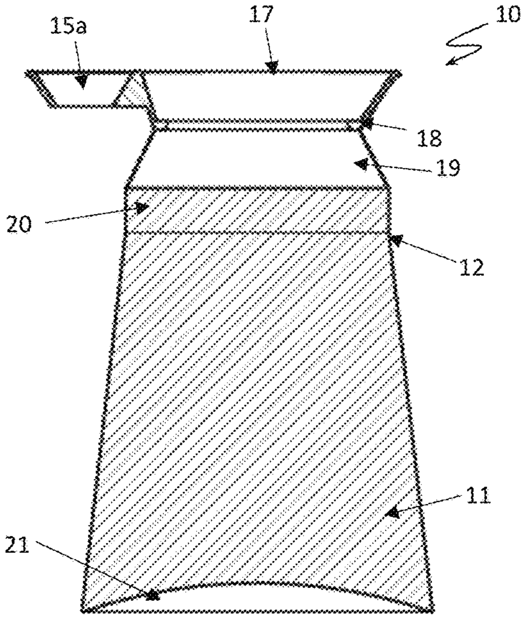
FIG. 4 is a cross-sectional view of the embodiment shown in FIG. 1A.

FIG. 4 is a cross-sectional view of the urine collection system (10) described in FIG. 1 showing the shape of the collection container (11). The receiving funnel (13) has conical body and wide upper rim (17) with flat profile. The body of the conical funnel (13) shown in FIG. 4 have straight walls that narrow toward the lower part with the exit hole/opening (18) of the funnel (13) that has a smaller diameter D2 than the diameter D1 at the opening (24) as shown in FIG. 6. The transition portion (19) of the collection system (10) connects the conical funnel to the mouth (20) of the collection container (11). In one embodiment, the transition portion (19) can be part of the top portion of the collection container (11) while in another embodiments the transitional portion (19) can extend downward from the lower part of the funnel (13) and can be part of the receiving funnel (13). FIGS. 1-6 illustrate example of the upper rim (17) elliptically shaped with a straight (flat) shape and integrated handle (14) for holding the urine collection system (11). The collection container (11) in the embodiment illustrated in FIGS. 1-6, has a pyramidal shape, with the circumference at the mouth (20) being smaller than the base (21) circumference, allowing the collection container (11) to stand upright when full.

Figure 5:
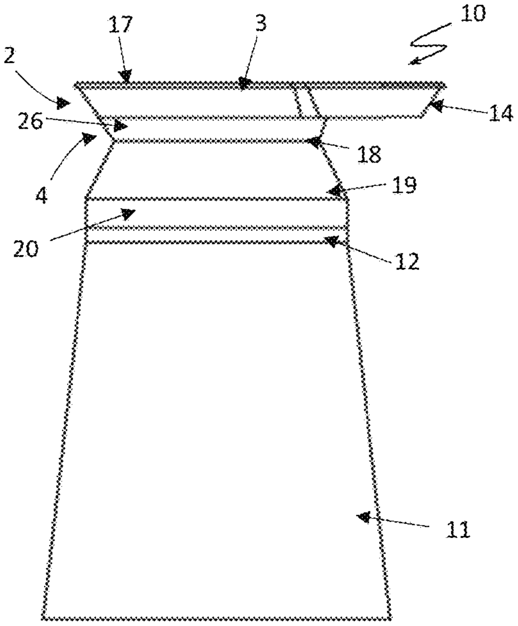
FIG. 5 is a side view of the embodiment shown in FIG. 1A.
Figure 6:
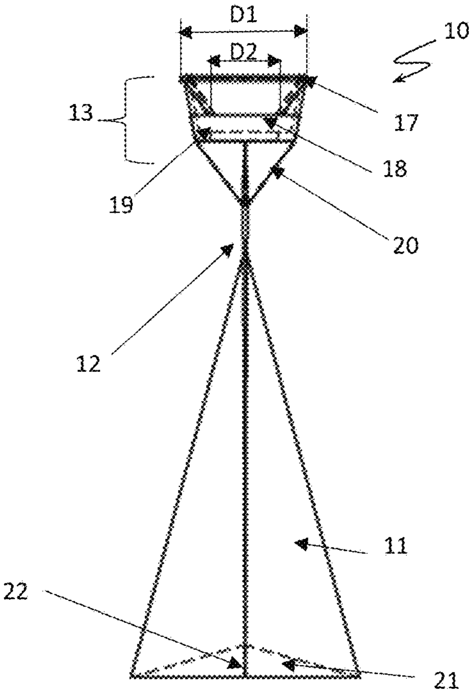
FIG. 6 is a cross-sectional side view of the embodiment shown in FIG. 1A showing a collecting container in closed position.

FIG. 5 is a side-view of the urine collection system (10) described in details with respect to FIGS. 1-4 herein above, showing clearly the upper part (2) with the ring-shaped body (3) and the lower part (4) of the receiving funnel (13).

FIG. 6 is a cross-sectional side view of the urine collection system (10) described in FIG. 1, showing the collection container (11) with a closure (12) in closed position, and a receiving funnel (13) with conical walls narrowing down from the rim (17) towards the lower part and exit opening (18). The conical funnel (13) is attached to the collection container (11) at the mouth (20). The transition portion (19) is extending from the lower part (4) of the funnel (13) and is enveloped by the top edge/mouth (20) of the collection container (11). The collection system (10) is positioned such that the rim (17) is pressed against the body so that the entrance opening (24) of the funnel (13) surrounds the genital parts of user and the urine coming out is injected into the funnel body (26) and funneled down by the sloped structure of the body (26) into the collection container (11).

FIGS. 7-12 show another embodiment of a urine collection system (100) that comprises a collection container (110) and a receiving funnel (120) connected to or integrated with the collection container (110). The collection container (110) has a square shape with a square shaped base (111), a first wall (117), a second wall (119) and two side walls (116) connected to the first and second walls (117) and (119) along respective side edges. The first, second and two side walls (117), (119) and (116) are connected to the base (111) along their respective lower edge forming the collection container (110) with square shape. The square base (111) attached to the enclosing walls (117), (119) and (116) define the inner cavity of the container (110) where the urine collected is contained within. The collection container (110) has an opening formed at a top edge (112) and a closure (113) positioned underneath and in proximity to the opening. A crease (130) can be formed at each of the side walls (116), forming a pleated fold (150) on each side wall (116) to allow the container (110) to be foldable and collapsible when empty. A pleated fold (150) is defined as an accordion style fold, which is composed of a series of alternating folds that create several similar-sized folding sections. In the illustrated embodiment of FIG. 7, there is only one pleated fold (150) formed in each of the side walls, however persons skilled in the art would understand that multiple folds (see FIG. 13) can be formed in each of the side walls without departing from the scope of the invention. In some embodiments, an additional crease (115) can be formed on the base (111), that is similar to the crease (22) in the collection container (11) shown in FIGS. 1-6, to fold the collection container (110) into collapsed and smaller size when not in use. In another embodiments, the additional crease (115) formed on the base (111) can be omitted and the collection container (110) can collapse/fold into smaller size when not in use without folding the square base (111). By having collection container (110) with pleated side walls (116), the volume of the collection container (110) can increase to a greater volume than the collection container (11) shown in FIGS. 1-6. In addition, the square base (111) of the container (110) allows the container to stand stable when full and hold a greater volume of liquid fluid than the collection container (11) with an oval-shaped base (21) shown in FIGS. 1-6. The collection container (110) can be made in various sizes similarly to the collection container (11) described herein above with respect to the collection system (10) illustrated in FIGS. 1-6. The closure (113), similar to the closure (12), is provided in proximity and downward from a top edge/mouth (112) of the collection container (110) to tightly close the container opening when the closure (113) is in a closed position.

The receiving funnel (120) has an upper part (102) having a ring-shaped body (103), an entrance opening (124) that can be elliptically shaped with an upper rim (127) formed along the entrance opening (124), and a lower part (104) forming a funnel body (126) extending downwardly and forming funnel conduit to direct the urine through the receiving funnel (120) into the collection container (110). The diameter of the body (126) at the entrance opening (124) is bigger than a diameter of the body (126) at its lower exit portion (118). The receiving funnel (120) and the entrance opening (124) can be sized and shaped to fit around female genitalia parts surrounding a perimetral region of all female genitalia parts. The handle (14) that can be connected/integrated with the receiving funnel (120) to help with positioning and holding firmly the urine collection system (100) while positioning the upper rim portion (127) against the user's body during use. The handle (14) can have the hole (**15*b***) that is shaped and sized as two-fingers hole, however the hole can be a single-finger hole or a three-finger hole, as described herein above, without departing from the scope of the invention.

The ring-shaped body (103) of the receiving funnel (120) can have a concave curved walls that curve inwardly at the middle (128) resulting in a cup-like structure, and gently slope downward towards the lower part (104). The exit opening (118) of the receiving funnel (120) is of a smaller diameter than at the entrance (124). Compared to the straight-walled conically shaped funnel body (26) shown in FIGS. 1-6, the concave shaped body (103) can receive a greater volume of liquid and can lower the risk of urine spraying back towards the user' body parts due to turbulent ejections hitting the body walls with force. The upper rim (127) can be ergonomically shaped and can have a curved profile to better fit curves of user's body surrounding their genital parts.

Similar and as described with respect to the collection system (10), the receiving funnel (120) and collection container (110) can be manufactured as an integrated element or it can be thermally bonded or glued together. In another embodiment, the receiving funnel (120) and the collection container (110) can be attached, for example using loops, zippers, or a male and female element that are locked together and can be detachably connected. The urine collection system (100), similarly as described above with respect to system (10), can be made of a biodegradable material and can be disposable. In other embodiments, the system (100) can be cleaned and reusable. In some implementations, one or both of the collection container (110) and conical funnel (120) can be reusable. In another implementations, one or both of the collection container (110) and conical funnel (120) can be disposable. The square-shaped collection container (110) can be used for a variety of volumes.

In some implementations, the collection system (100) can be use as medical lab urine sample collection system with sample size of about 120 millilitres to up to a size of about 500-milliliter volume. The integrated ergonomic handle (14) is configured to allow the user to grip the collection system (100) and position the rim of the funnel to the anterior portion of the vagina, around the labia majore, to prevent spilling due to increased weight in the collection container. The collection container (110) may or may not have a closure (113). In one embodiment the seal (113) is comprised of an interlocking mechanism to seal the collection container. In one embodiment, the interlocking mechanism is composed of a male and female element that are manually or mechanistically locked together to create a seal. In another embodiment, the interlocking mechanism is comprised of one or several zipper sealed closures to ensure a leak proof seal. In another embodiment where the sample is immediately disposed of, the collection container (110) does not have a seal (113).

Figure 7:
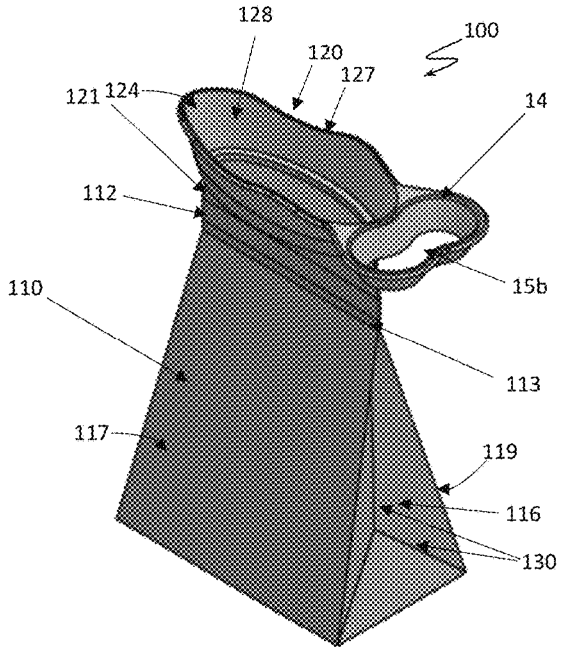
FIG. 7 is a perspective view of an example of a female urine collection system according to another embodiment of the present invention.
Figure 8:
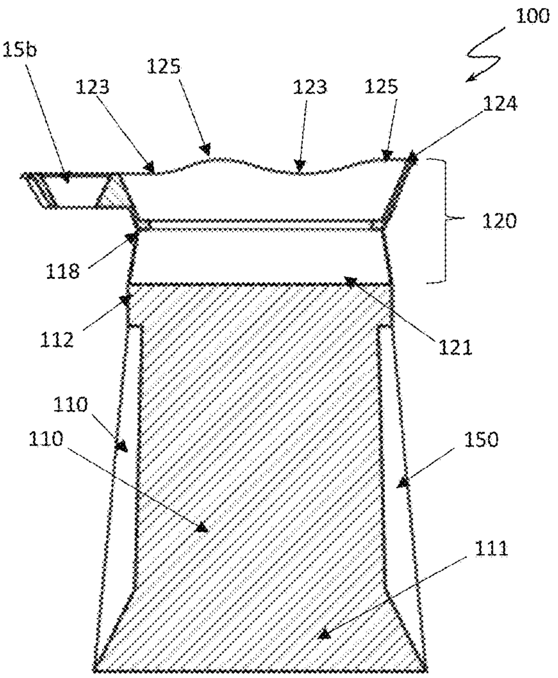
FIG. 8 is a cross-sectional view of the embodiment shown in FIG. 7.

FIG. 8 is a cross-sectional view of the urine collection system (100) described in FIG. 7 showing the curved upper rim (127) that contours to the body of the user's genitalia to better fit to the body parts and for increased comfort during use. In the curved design shown in FIG. 8, there are two peaks (125) with first peak formed at the anterior portion/end and second peak formed at the middle portion of the funnel rim (127), and two valleys (123), where first valley is formed at the posterior portion and second valley is formed at the middle portion of the rim (127). The collection container (110) has a square shape at the base (111) and two pleats or folds (150) formed in each of the side walls (116) for folding the container (110) to a smaller size when empty.

Figure 9:
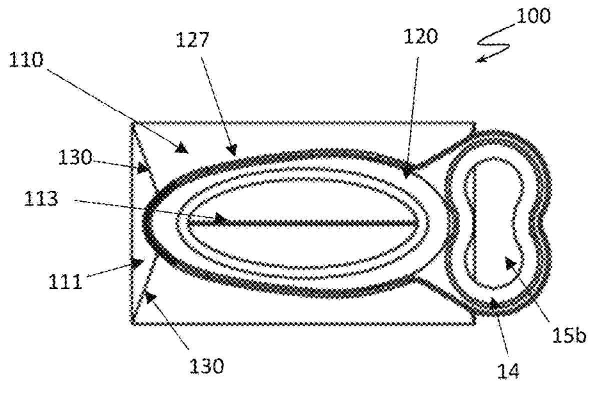
FIG. 9 is a top view of the embodiment shown in FIG. 7.

FIG. 9 show a top view of the urinal system (100) described in FIG. 7. As shown in FIG. 9 the receiving funnel (120) can have an elliptical shape. The handle (14) has double-fingers hole (**15*b*) design for ergonomic grip. The urinal collection system (100) further shows the closure (113) in a closed position when in the collection container (110) is sealed, as illustrated by the line (113**) which represents the closure in closed position.

Figure 10:
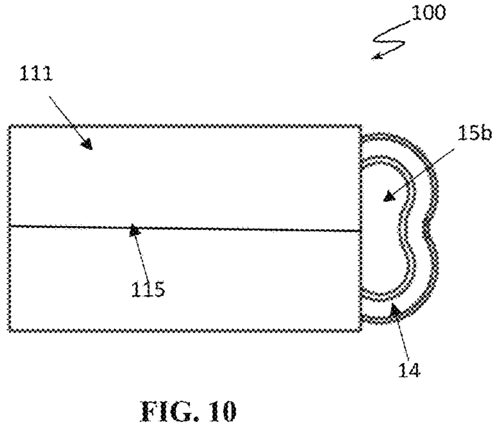
FIG. 10 is a bottom view of the embodiment shown in FIG. 7.

FIG. 10 is a bottom view of the urinal collection system (100) described in FIG. 7. The collection container (110) has a square shape base (111) to increase the volume of the of the collection container (110). The crease (115) can also be provided to allow easy folding of the container (110).

Figure 11:
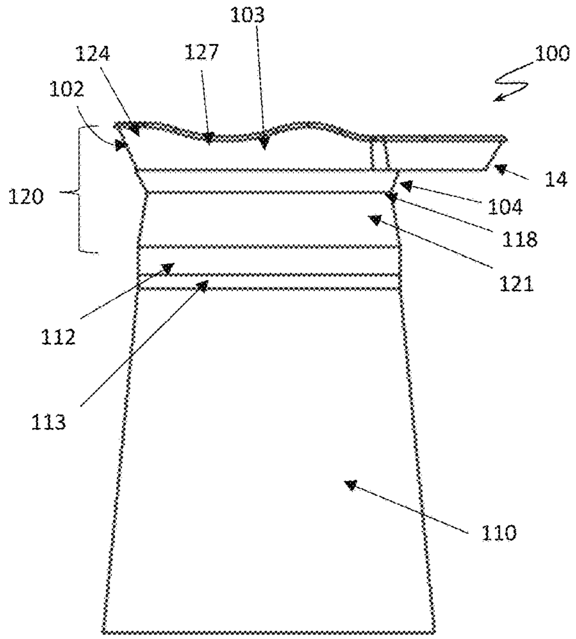
FIG. 11 is a side view of the embodiment shown in FIG. 7.

FIG. 11 is a side-view of the urine collection system (100) described in detail with respect to FIGS. 7-10 herein above, showing the upper part (102) with the ring-shaped concave body (103) and the lower part (104) of the receiving funnel (120).

Figure 12:
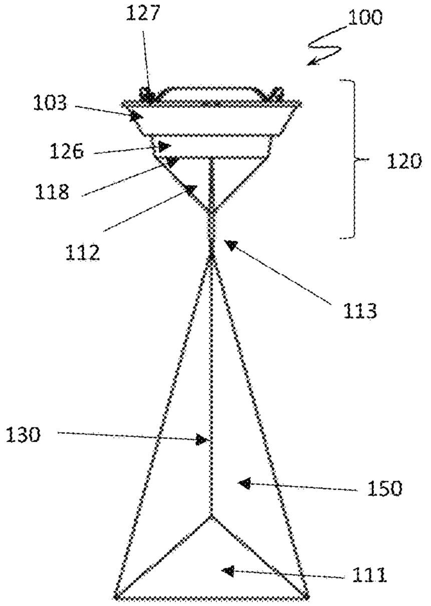
FIG. 12 is a cross-sectional side view of the embodiment shown in FIG. 7 showing a collecting container in closed position.

FIG. 12 is a cross-sectional side view of the urine collection system (100) described in FIG. 7, showing the collection container (110) with a closure (113) in closed position, and a receiving funnel (120) with concaved, curving inwardly, walls narrowing from the rim (127) forming cup-like body (103) and the funnel body (126) narrowing towards the lower part and the exit opening (118). The funnel (120) is attached to the collection container (110) at the mouth (112). The closure (113) of the collection container (110) is illustrated in its closed position.

FIGS. 13-18 illustrate another embodiment of a urine collection system (1000) that comprises a collection container (1100) and a receiving funnel (1200) connected to the collection container (1100). The collection container (1100) can be flexible and can have several different sizes and shapes. Similar to the collection container (110) shown in FIGS. 7-12, the collection container (1100) has a wider square base (1110), compared to base (111) of embodiment shown in FIGS. 7-12. The base (1110) is attached to walls (1112) with a pleated design (1140). An opening is formed at a top edge (1120) of the collection container (1110). The base (1110) and the walls (1112) define the collection cavity of the container (1100) sized to collect liquid fluid. The collection container (1100), similarly to the container (110) has four walls (1112), and the pleated style folds (1140) are formed in the two side walls (1112*a*) that allow the user to collapse the container (1110) to a minimal size. A pleated fold is defined as an accordion style fold, which is composed of a series of alternating folds that create several similar-sized sections. The expandable collection container (1100) having multiple folds (1140) can hold large volumes of liquids up to 650-milliliters. The square-based pyramidical shape increases the sample storage capacity compared to a container (11) with an oval-shaped base (21) shown in FIG. 1 and allows the collection container to stand with greater stability when full.

The receiving funnel (1200) can have an upper part (1202) with a ring-shaped body (1203), an upper rim (1220) formed along an entrance opening and a a lower part (1204) forming a funnel body (1226) extending downwardly and forming funnel conduit to direct the urine through the receiving funnel (1200). The ring-shaped body (1203) can have a convex shape which extends outwardly from the upper rim (1220) into a wide middle portion (1230) which then slopes and narrows in the lower part (1204) and a funnel exit opening (1210). The bottom end where the exit opening (1210) is formed of the lower part (1204) of the receiving funnel (1200) is joined to the top/mouth (1120) of the collection container (1100). Therefore, the shape of the ring-shaped body (1203) of the funnel (1200) is cup-like or a barrel-like, with walls that extends out right under the rim (1220) to prevent the incoming flow of urine to hit such wall and bounce back toward the exposed parts of the user, keeping the exposed parts of the user clean and dry without need to wipe them dry after use. The upper rim (1220) can have a curved design to better match/fit to the curves or contours to the body of the user surrounding user's genitalia.

The urine collection system (1000) also comprises handle (14) extending outwardly from the body (1203) of the receiving funnel (1200). The handle (14) can further comprise hole that can be designed as any of a single, double or three-fingers-hole as described herein above. The handle (14) shown in the embodiment of the collection system (1000) has three-fingers designed hole (15*c*) meaning that three fingers can be inserted in the hole (15*c*) simultaneously at the same time to hold the system (1000) during use. In some embodiments the handle (14) can have three, or more or less, independent/separate holes for user to insert finger through each separate hole. The receiving funnel (1200) and the collection container (1100) can be made as an integrated structure by injection molding or 3D printing or can be thermally bonded or glued together. In some implementations, the receiving funnel (1200) can be detachably joined to the collection container (1100). For example, the receiving funnel (1200) and the collection container (1100) can be reversibly attached, using for example two-parts connectors such as, hooks and loops, zippers, Velcro™ fasteners, zipper seal or any other fastener with male and female elements interconnecting together. The urine collection system (1000) can be disposable, reusable or some parts of the system (1000) can be reusable while other disposable as described herein above.

The collection container (1100) can comprise a closure (1130) that can be used to open and close the top/mouth (1120) of the container (1100). The closure (1130) can be a two-part connector with an interlocking mechanism positioned down from the mouth (1120) and configured to tightly seal the collection container (1100) when the closure (1130) is in closed position. For example, the closure (1130) can be a single zipper seal or multiple zipper seals to ensure a tight, leak proof, seal when the closure (1130) is in closed position.

Figure 13:
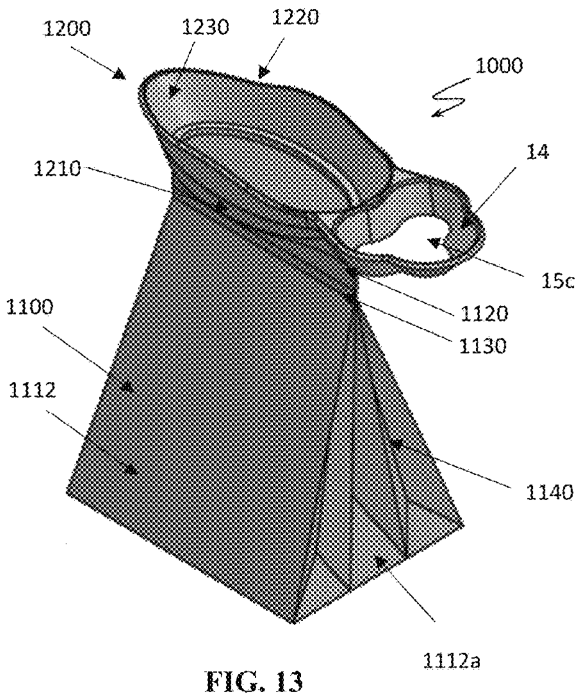
FIG. 13 is a perspective view of an example of a female urine collection system according to yet another embodiment of the present invention.
Figure 14:
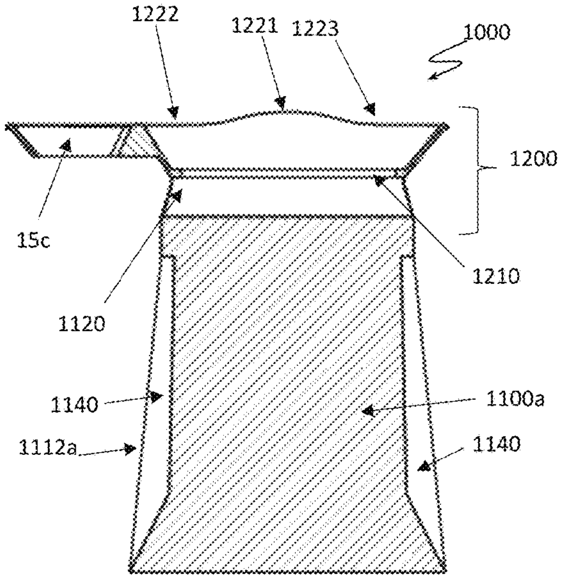
FIG. 14 is a cross-sectional view of the embodiment shown in FIG. 13.

FIG. 14 is a cross-section view of the urine collection system (1000) described in FIG. 13 showing a cross-section of the container (1100) with the cavity (1100*a*) and the folds 1140 formed in each of the two opposite side walls (1112*a*). The receiving funnel (1200) has curved upper rim (1220) and body (1226) that widens in the middle (1230) and then narrows towards at the lower part (1204) where it is attached to the collection container (1100). The curved upper rim (1220) can have one peak (1221) formed at the middle portion of the rim (1220) and two valleys, where a first valley (1222) is formed at the posterior end and a second valley (1223) is formed at the anterior end of the rim (1220).

Figure 15:
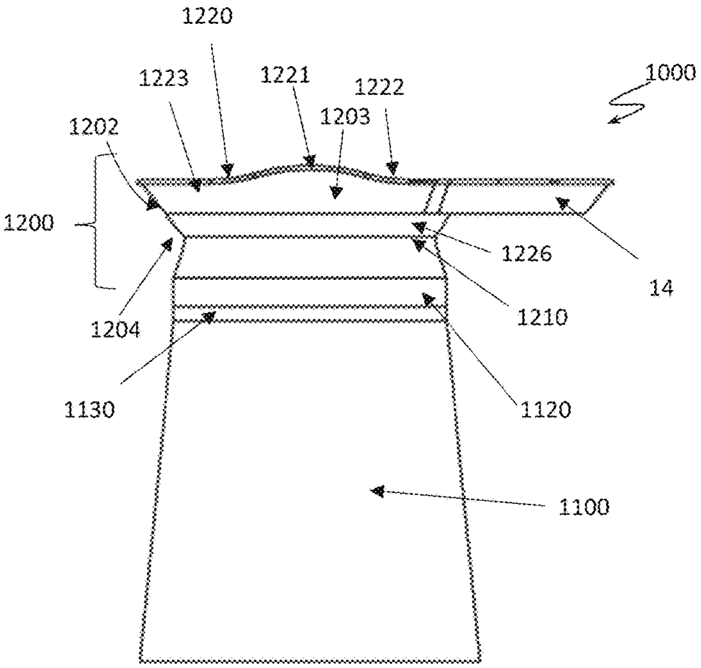
FIG. 15 is a side view of the embodiment shown in FIG. 13.

FIG. 15 is a side-view of the urinal collection system (1000) showing the curved upper rim (1220) with one peak (1221) located in the middle section of the rim, and two valleys at the anterior (1223) and posterior section (1222) of the rim (1220). The body (1226) of the funnel can have barrel-like shape with widening middle portion extending downwardly and outwardly from rim (1220) followed by sloping downwardly and inwardly narrowing the funnel toward the lower portion (1204) directing the urine towards the exit opening (1210) and into the urine collection container (1100) to which the funnel (1200) is attached.

Figure 16:
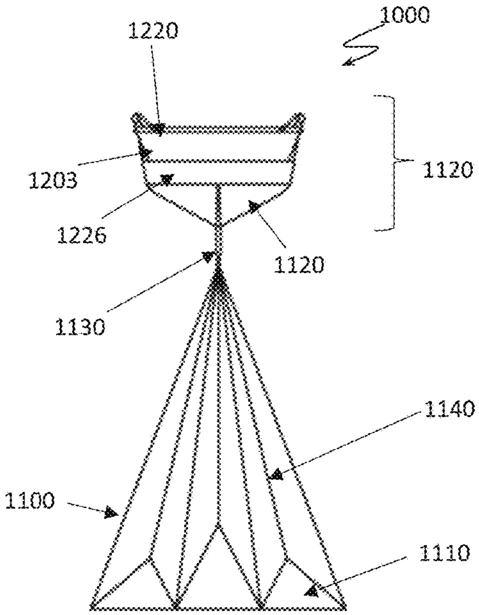
FIG. 16 is a cross-sectional side view of the embodiment shown in FIG. 13 showing a collecting container in closed position.

FIG. 16 is a side cross-sectional view of the urine collection system (1000) showing the collection container (1100) with the closure (1130) in closed position to keep the inner cavity of the container (1100) tightly closed to prevent any spill out of the container. The collection container has pleated style folds (1140) that allow the user to collapse the container to a smaller size. The body (1203) of the receiving funnel (1200) has convex shape and curved upper rim (1220).

Figure 17:
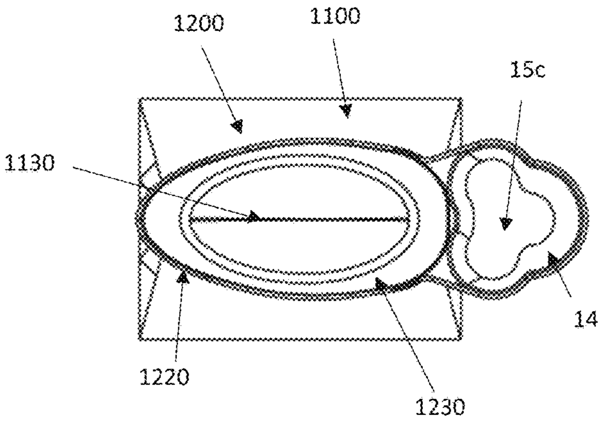
FIG. 17 is a top view of the embodiment shown in FIG. 13.

FIG. 17 is a top view of the urine collection system (1000) with the receiving funnel (1200), the collection container (1100) and the handle (14) with the three-fingers hole (15*c*) designed for ergonomic grip. The collection container (1100) is in a sealed position, as demonstrated by the line (1130) which represents the closure.

Figure 18:
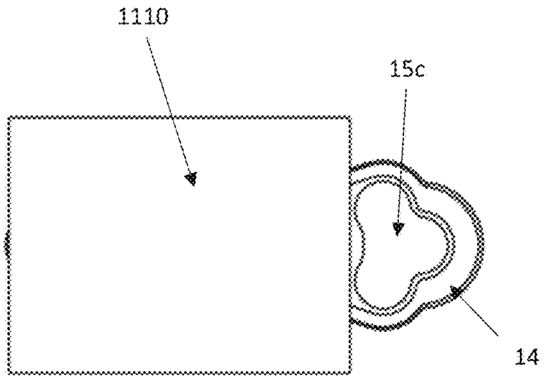
FIG. 18 is a bottom view of the embodiment shown in FIG. 13.
Figure 19A:
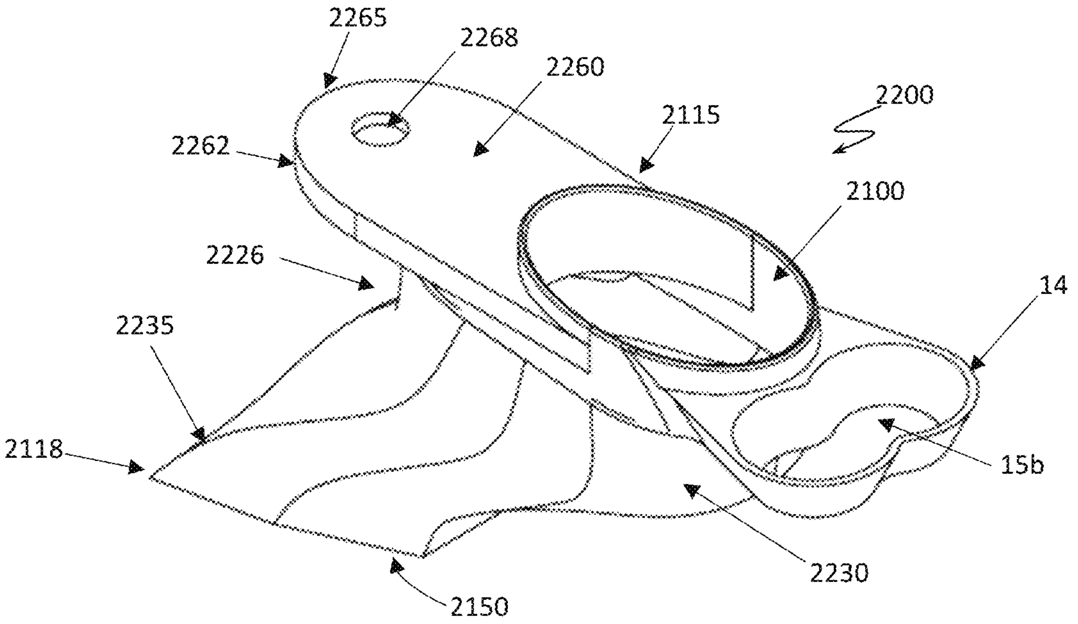
FIG. 19A is a perspective view of an example of a receiving funnel of an embodiment of a female urine collection system configured to be used when a user is in a seated or laid down position.
Figure 19B:
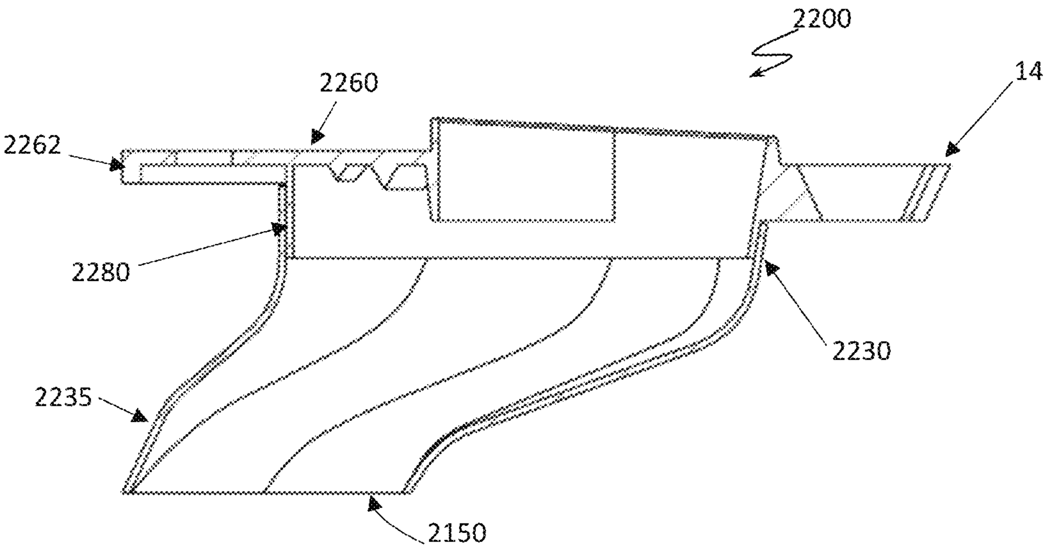
FIG. 19B is a cross-sectional side view of the receiving funnel shown in FIG. 19A.
Figure 19C:
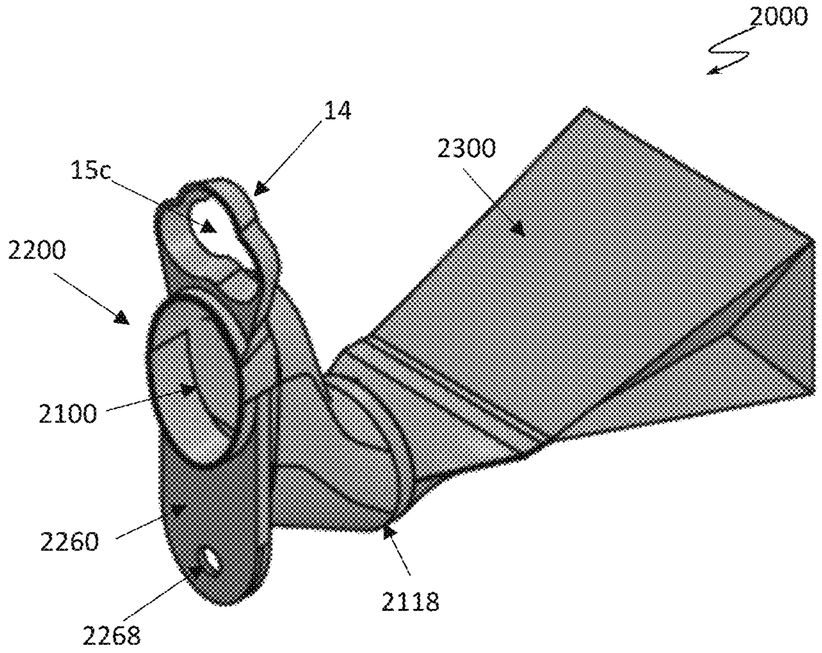
FIG. 19C is a perspective view of a female urine collection system showing the receiving funnel of FIG. 19A joiner with a collection container.
Figure 19D:
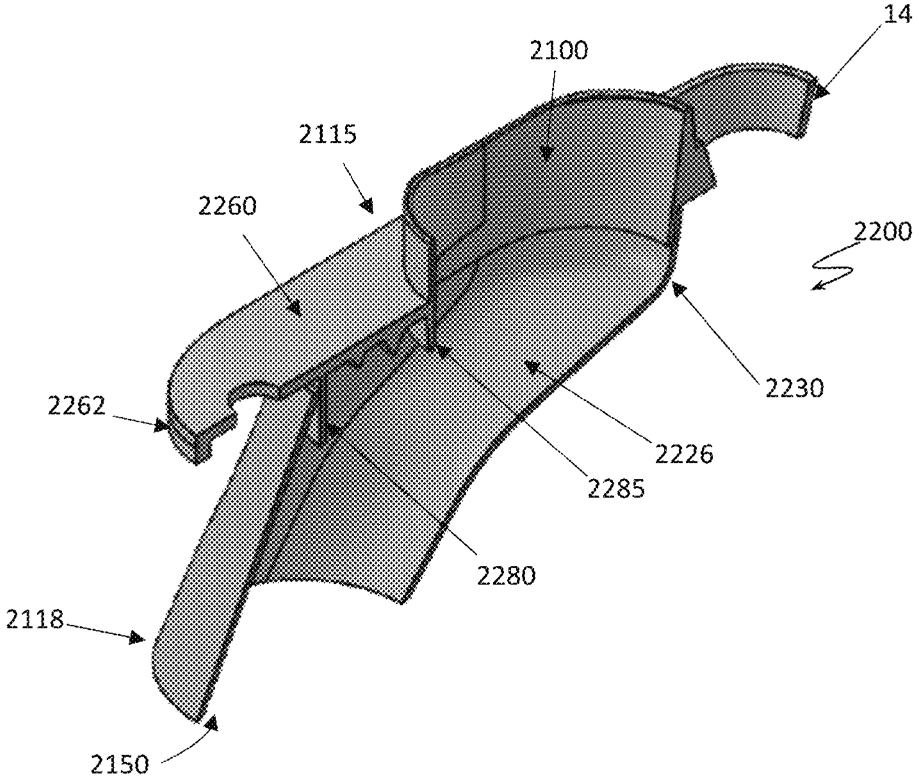
FIG. 19D is a perspective cross-sectional view of the receiving funnel shown in FIG. 19A.

FIG. 18 is a bottom view of the urine collection system (1000) showing the square shaped base (1110) and the handle (14) with the three-fingers hole (15*c*).

FIGS. 19A-19D show another embodiment of a urine collection system (2000) with a receiving funnel (2200) configured to be used for users in lay down position or seated/half-seated position. The receiving funnel (2200) has an entrance opening (2100) formed at an upper part (2115), an exit opening (2150) formed at a lower part (2118) and a body (2226) extending between the entrance opening (2100) and the exit opening (2150). The body (2226) has a curved shape with upper part (2230) that extends from the entrance opening (2100) forming the upper funnel chamber and a lower curving funnel part (2235). The upper funnel chamber (2230) can have a straight conical walls, a concave (cup-like) shape or convex (barrel-like) shape as described herein before with respect to receiving funnel (13), (120) and (1220), respectively. The diameter/volume of the upper part (2230) is greater than the diameter/volume of the lover part (2235). The curved funnel body (2226) is configured so that the receiving funnel can be used when the user is in lay down position, such as for example, when the user is bedridden or cannot stand easily. The upper part (2115) of the receiving funnel (2200) further comprises an extending lip (2260) that is extending our of the entrance opening rim at the anterior end of the funnel's upper part. The extending lip has a peripheral edge forming a support surface such that the extending lip (2260) is supported on the bed with the edge surface (2262) formed at the anterior end (2265) positioned on the bed surface. The extending lip (2260) acts as lever to provide height/distance from the entrance opening (2100). The extending lip/lever (2260) along with the funnel body (2226) are designed to provide slope surrounding the entrance opening (2100) allowing the discharged urine to flow downwardly directed by the funnel curved body into a collection container. When in use, the user or the caregiver can position the receiving funnel (2200) such that the rim of the entrance opening (2100) surrounds the genitalia parts while the edge surface (2262) of the extending lip (2260) is supported by the bed surface (see FIG. 26B). A handle 14 can be connected to the body (2226) at the posterior end. The handle can have finger opening 15 as described herein before. An additional finger opening (2268) can also be provided which can be formed in the body of the extending lip (2260) to help the user or the caregiver to position and/or remove the receiving funnel (2200) from the user.

The receiving funnel (2200) can further comprise at least one deflector barrier (2280) to prevent the urine flowing back to contact the female parts. The at least one deflector barrier (2280) can be formed at the lower level of the upper funnel chamber (2230). In one embodiment, two deflecting barriers can be provided. For example, a first deflecting barrier (2280) can be formed at at the lower level of the upper funnel chamber (2230) and a second deflecting barrier (2285) can be located underneath of the entrance opening ring (2100) for safety reasons in case of urine overflow (see FIG. 19D). The first and the second deflecting barriers (2280) and (2285) can both have a ring shape (e.g., elliptical ring) that extend away from an inner surface of the upper part (2115) into the interior of the funnel body (2226). A collection container (2300) can be attached to the lower part 2118 of the receiving funnel (2200). During use the collection container (2300) can rest over the bed, between user legs, as shown in FIG. 26B, such that no body part is pressing over the collection container (2300). In one embodiment, the collection container (2300) can be the bedpan that is separate from the receiving funnel (2200) and the lower exit opening (2150) can be in fluid communication with the inner cavity of the bedpan so that the urine flowing out of the funnel is collected in the bedpan. The additional finger opening (2268) and the handle (14) can be used to position the receiving funnel and to firmly apply pressure against user body to avoid any spillage. For example, the handheld grabbing holes 15 in the handle 14 can be designed for inserting one to three fingers to make enough pressure to fit the entrance opening (2100) around the vagina and the additional finger opening (2268) formed on the opposite side can facilitate to grab the urine collection device (2000) with the other hand when female have finished urinating and the urine is collected in the collection container. The ergonomic female urinal collection system (2000) works in angular way on the bed position connecting the lower part (2118) of the receiving funnel (2200) with the upper part of angularly positioned collecting container (2300) which is located below of the first deflector barrier level (2280) to avoid spillage when the urine level cope with the maximum capacity of the collection container. In addition, the second deflector barrier (2285) is designed as a restricting area to avoid urine to come back to the opening (2100) in extreme case overflow and involuntary erratic movement.

The present invention can provide, for bedridden female, urine collection system (2000) that can assist females to urinate while avoiding direct contact with public bed pan seats when they are bedridden in clinics, hospitals and home care facilities minimizing unwanted potential risk of getting cross infections.

Figure 20A:
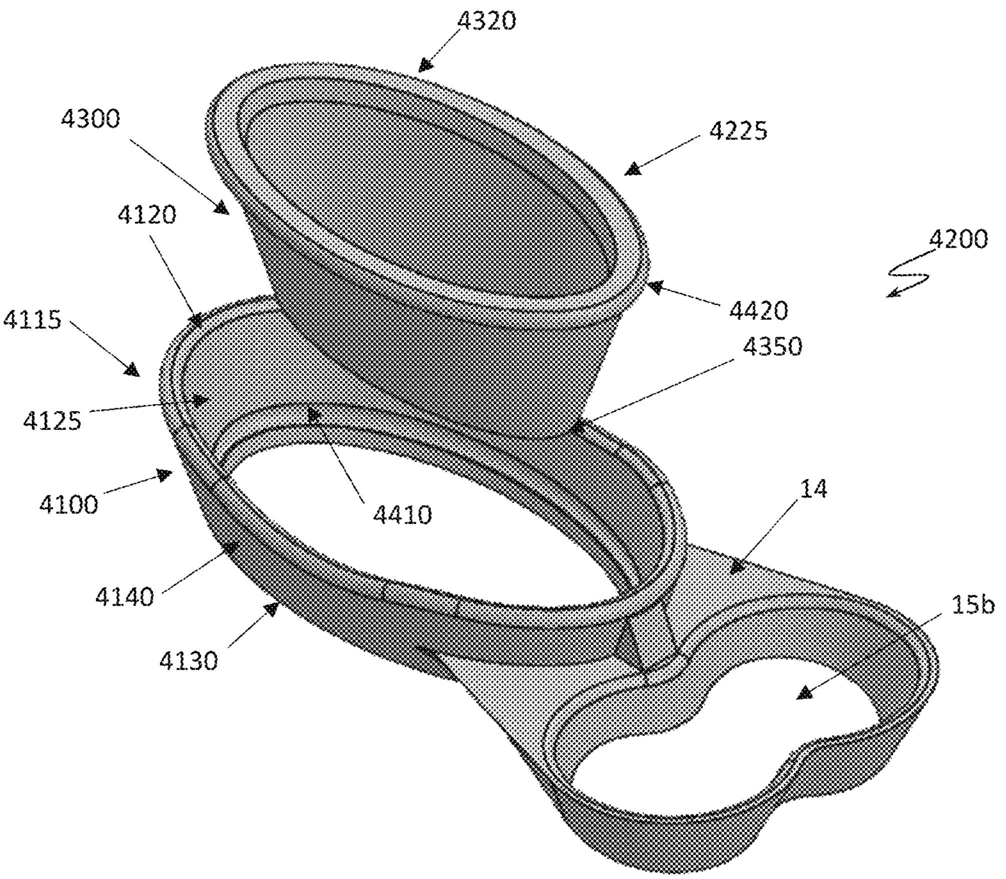
FIG. 20A is a perspective view of an example of a detachable receiving funnel of an embodiment of a female urine collection system in a detached position.
Figure 20B:
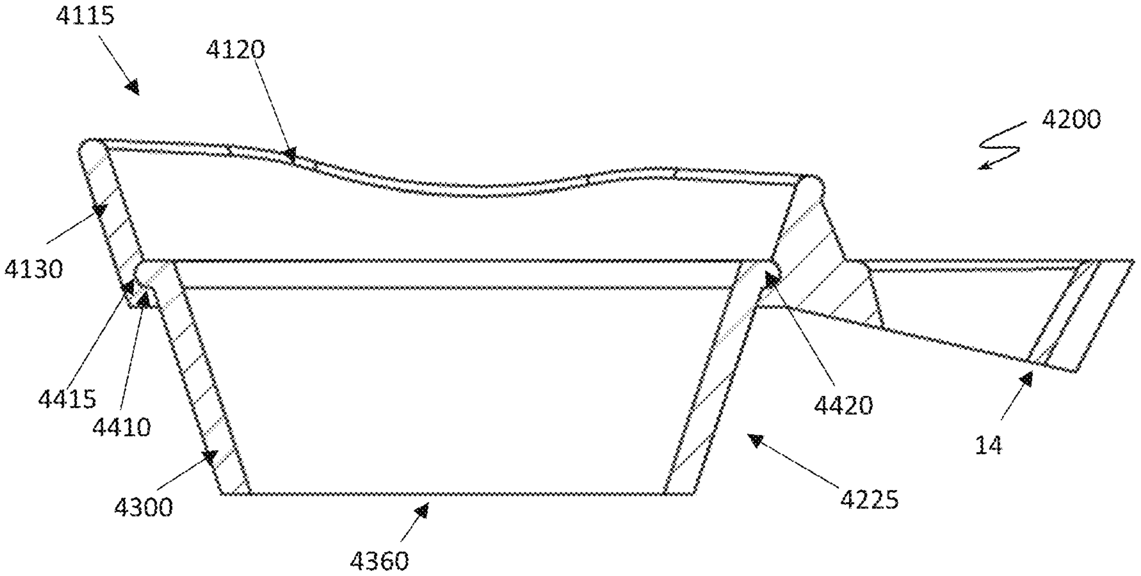
FIG. 20B is a cross-sectional side view of the detachable receiving funnel shown in FIG. 20A in an attached position.
Figure 20C:
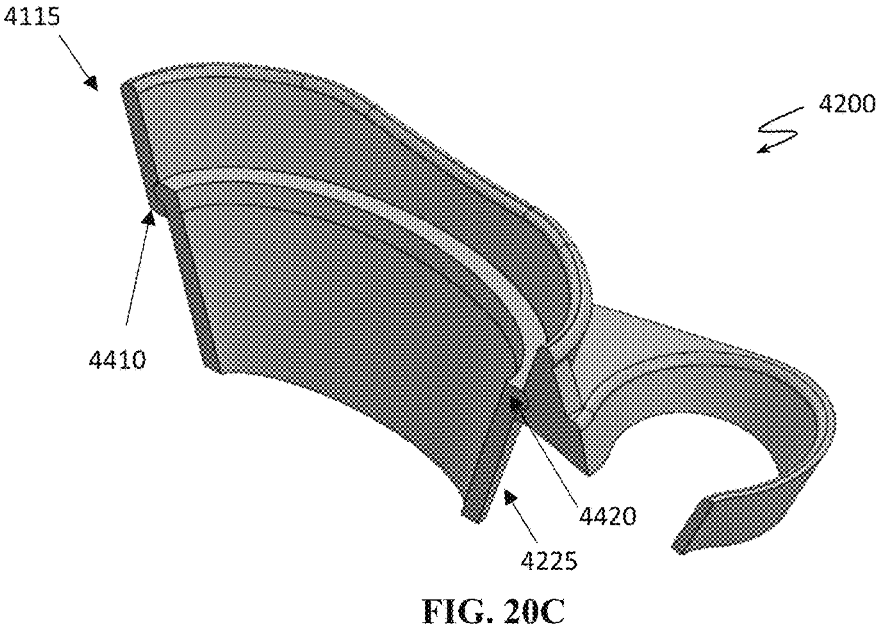
FIG. 20C is a perspective cross-sectional view of the detachable receiving funnel shown in FIG. 20A in an attached position.

FIGS. 20A-20C show another embodiment of a receiving funnel (4200) that comprises an upper part (4115) and a lower part (4225). The upper part (4115) and the lower part (4225) can be detachably connected such that they can be attached when in use and easily detached when not in use. In one implementation, the upper part (4115) can be reusable while the lower part (4225) can be discarded, and in some implementations, recycled after the use. The upper part (4115) has a ring-shaped body (4100) with an upper rim (4120) formed at a top edge defining an entrance opening (4125), a lower rim (4130) formed at a bottom edge and a side wall (4140) extending between the upper rim (4120) and the lower rim (4130). The lower part (4225) forms a funnel body (4300) with an upper edge (4320) and a lower edge (4350) defining an exit opening (4360) of the receiving funnel (4200). A two-part connector is provided to detachably connect the upper part (4115) and the lower part (4225). The two-part connector can comprise a ledge (4410) formed at the upper part (4115) and a flange (4420) formed at the lower part (4225). The ledge (4410) extends inwardly of the lower rim (4130) of the upper part (4115). The flange (4420) extends outwardly from the upper edge (4320) of the lower part (4225). The upper part (4115) and the lower part (4225) are configured such that when they are in an attached position the flange (4420) steadily rests on the ledge (4410) and the funnel body (4300) of the lower part (4225) extends downwardly from the bottom edge of the upper part (4115). In one implementation, the ledge (4410) can further wave a recess (4415) formed in the side wall (4130) sized and shaped to receive at least a portion of the flange (4420). The ring-shaped body (4100) of the upper part (4115) can have a concave (cup-like) shape side wall (4140). In other embodiments, the ring-shaped body (4100) of the upper part (4115) can have straight conical wall, or convex (barrel-like) shape wall as described herein before with respect to receiving funnel (13) and (1220), respectively. A handle (14) with finger opening (15) can be connected to the upper part (4115) as described herein above.

Figure 21A:
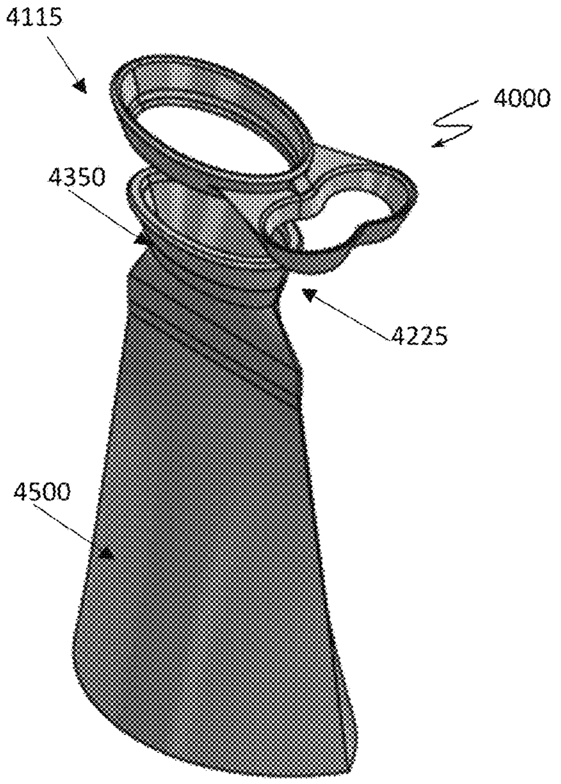
FIG. 21A is a perspective view of an example of a female urine collection with a detachable receiving funnel in a detached position.
Figure 21B:
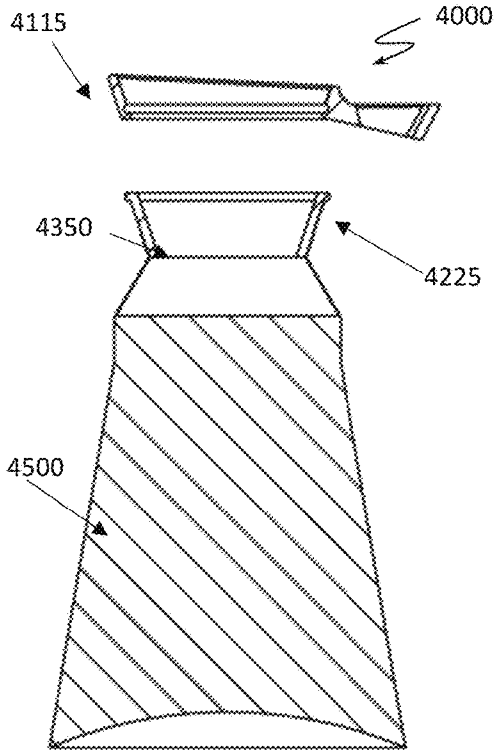
FIG. 21B is a cross-sectional side view of the female urine collection shown in FIG. 21A.

FIGS. 21A-21B show an embodiment of a urine collection system (4000) with the receiving funnel (4200), as described with respect to FIGS. 20A-20C, in a detached positioned with the upper part (4115) separated from the lower part (4225). A collection container (4500), as described herein above, can be attached to the lower part of the funnel body (4300) of the lower part (4225) of the receiving funnel (4200). In some implementations, after the use when urine is collected in the collection container (4500), the upper part (4115) can be disconnected from the lower part (4225) and it can be reuse by detaching it to another lower part (4225). The used collection container (4500) together with the lower part (4225) of the receiving funnel (4200), and after the urine is disposed, can be folded and discarded as waste.

Figure 22A:
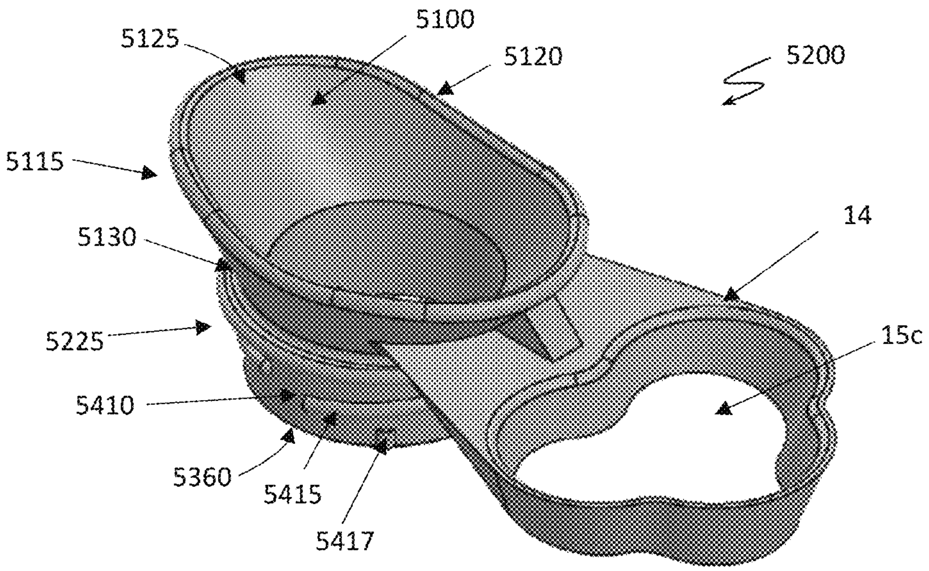
FIG. 22A is a perspective view of another example of a detachable receiving funnel of an embodiment of a female urine collection system in a detached position.
Figure 22B:
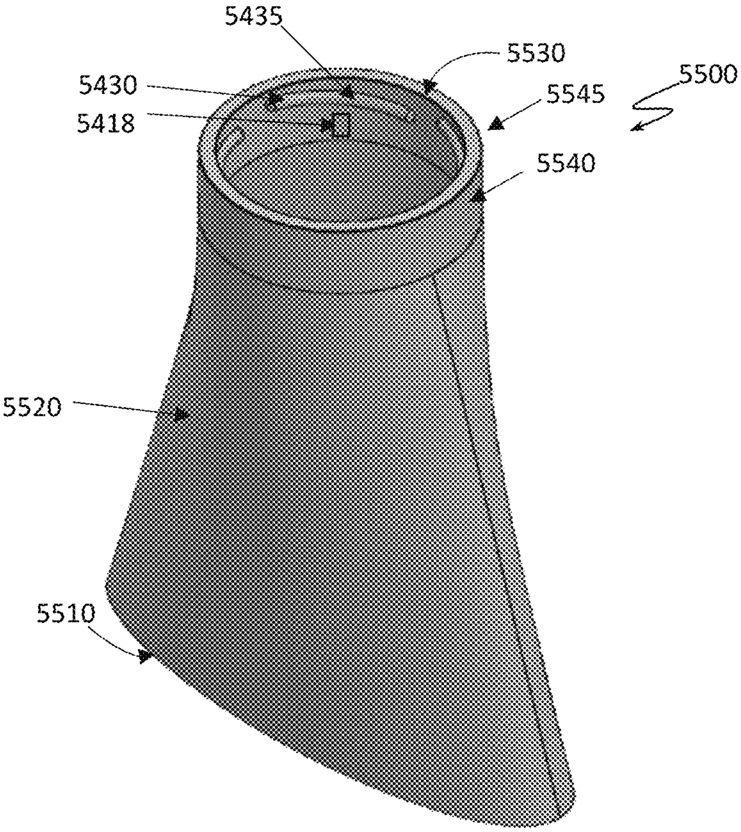
FIG. 22B is a perspective view of an example of a detachable collecting container.

FIGS. 22A-22D show another embodiment of a urine collection system having a detachable receiving funnel (5200) and a detachable collection container (5500). FIG. 22A shows the receiving funnel (5200) that comprises an upper part (5115) and a lower part (5225). The upper part (5115) and the lower part (5225) can be detachably connected similar to the receiving funnel (4200) shown in FIGS. 20A-20C or can be joined in an integral single piece. The upper part (5115) has a ring-shaped body (5100) with an upper rim (5120) formed at a top edge defining an entrance opening (5125), a lower rim (5130) formed at a bottom edge and a side wall (5140) extending between the upper rim (5120) and the lower rim (5130). The lower part (5225) forms a funnel body (5300) with an upper edge (5320) and a lower edge (5350) defining an exit opening (5360) of the receiving funnel (5200). The ring-shaped body (5100) of the upper part (5115) can have a concave (cup-like) shape side wall (5140). In other embodiments, the ring-shaped body (5100) of the upper part (5115) can have straight conical wall, or convex (barrel-like) shape wall as described herein before with respect to receiving funnel (13) and (1220), respectively. A handle (14) with finger opening (15) can be connected to the receiving funnel (5200) as described herein above. FIG. 22B illustrates a collection container (5500) that is detachably connected to the lower part (5225) of the receiving funnel (5200). The detachable collection container (5500) can be similar to the collection container (11), (110), (1100), (2300) or (4500) described herein above. The collection container (5500) comprises a base (5510) and a side wall 5520) extending upward from the base (5510) creating an inner cavity configured to receive and contain the urine collected during use. An opening (5530) is formed at a mouth (5540) at a top edge (5545) of the collection container (5500) to provide access to the inner cavity of the collection container (5500).

Figure 22C:
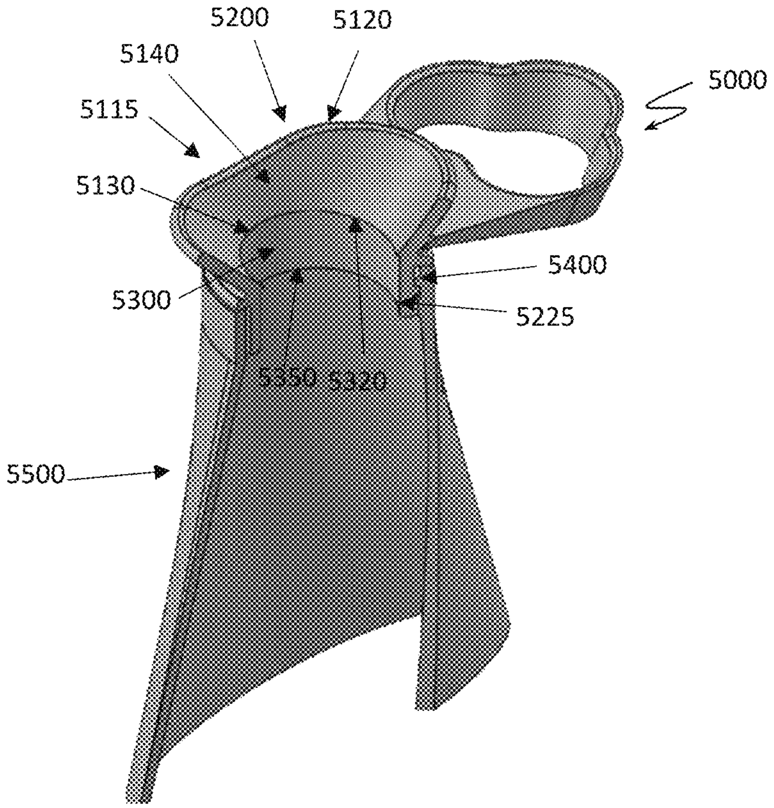
FIG. 22C is a cross-sectional side view of a female urine collection system with the detachable receiving funnel shown in FIG. 22A and the detachable collecting container shown in FIG. 22B in an attached position.
Figure 22D:
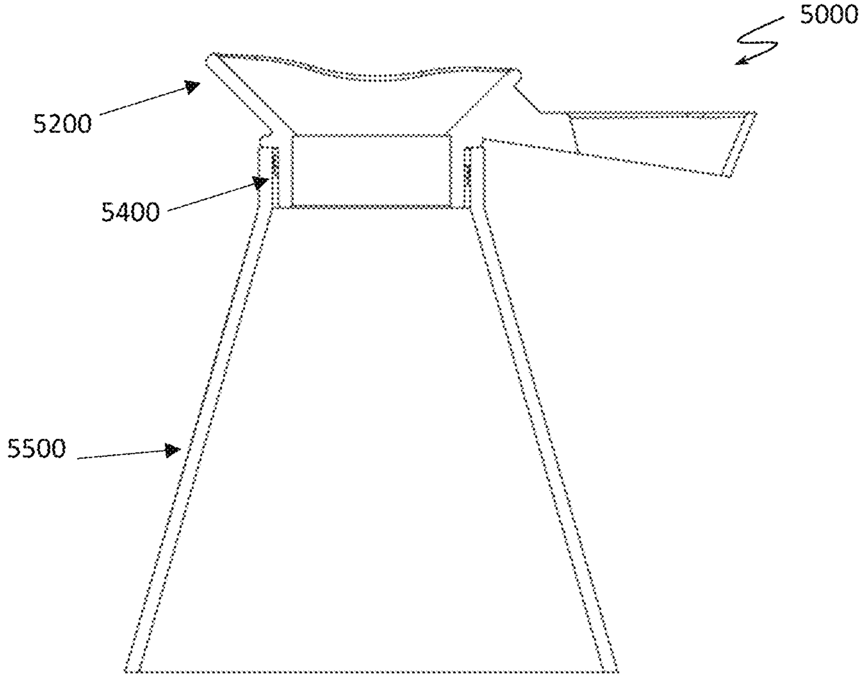
FIG. 22D is a cross-sectional side view of the female urine collection system shown in FIG. 22C in an attached position.

A two-part connector (5400) is provided to detachably connect the receiving funnel (5200) and the collecting container (5500). The two-part connector (5400) can have a first connector thread (5410) formed at the receiving funnel (5200) and a second connector thread (5430) formed at the collection container (5500). The two-part connector (5400) can further comprise a lock system (5417/5418) located at the lower part of receiving funnel and the upper part of collecting container. The lock system can be, for example a press-on and twist-off lock system, which can have at least one first locking element (5417) located at the lower part of receiving funnel (5200) and at least one second locking element (5418) located at the upper part of the collecting container (5500). The first connector thread (5410) can comprise number of ridges (5415) protruding outward from the periphery of the funnel body (5300) outer surface. The second connector thread (5430) can comprise number of ridges (5435) protruding away from an inner surface periphery of the mouth (5540) of the collection container (5500). The protruding ridges (5415) of the first connector (5410) and the protruding ridges (5435) of the second connector (5430) can be angled and have edges designed and configured to slide one between another when the receiving funnel (5200) is threaded into the collection container (5500). The at least one first locking element (5417) can be a lug that is protruding from the periphery of the funnel body (5300) in proximity to its lower edge (5350) and the at least one second locking element (5418) can be an indentation (5418) formed in the inner surface of the lower part of the mouth (5540) which is designed and configured to engage with the lug (5417), such that when the receiving funnel (5200) is threaded into the collection container (5500), the ridges (5415) slide between the ridges (5435) till the at least one lug (5417) fit into the indentation (5435) to securely lock the funnel (5200) to the container (5500). Plurality of lugs (5417) and corresponding indentations (5418) can be provided as part of the locking system to prevent the connectors (5410) and (5430) when threaded to be detached accidently during usage. In order to attached together the receiving funnel (5200) to the collection container (5500), the receiving funnel (5200) can be pressed in the mouth (5540) of the collection container (5500) and twisted to the right (as an example) in order for the ridges (5415) to slide between the ridges (5435) until at least one lug (5417) engages with the at least one indentation (5418) to hold the receiving funnel (5200) securely connected to the collection container (5500) as shown in FIGS. 22C and 22D. In order to detach (and remove) the receiving funnel (5200) from the collection container (5500), the receiving funnel (5200) is twisted to the left such that the lug (5417) disengage the indentation (5418) and the ridges (5415) slide away from ridges (5435) until they are clear to pull the funnel (5200) up and detached from the container (5500).

Figure 23A:
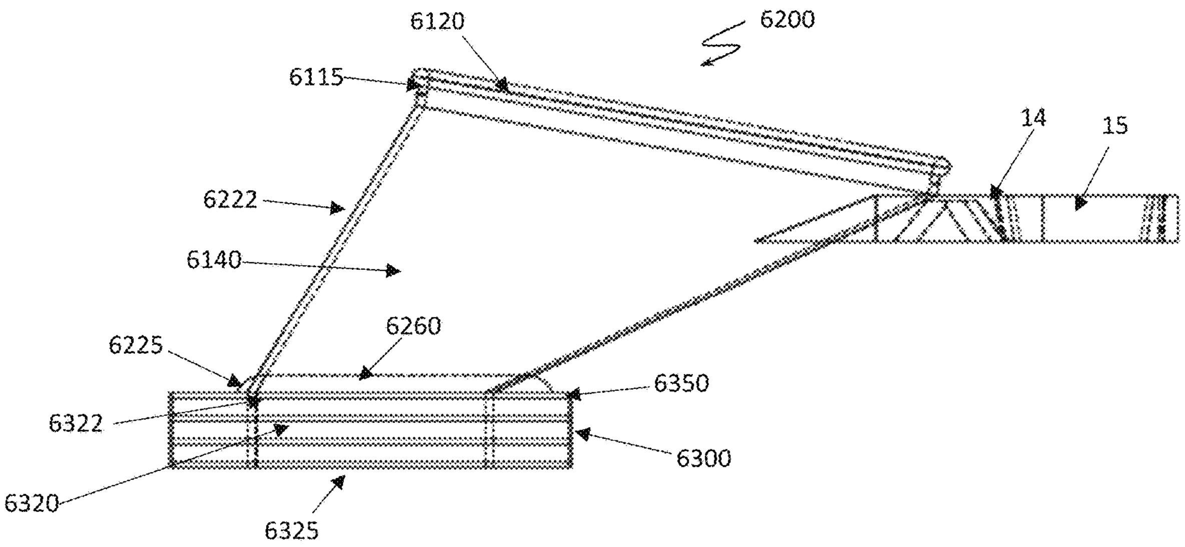
FIG. 23A is a side view of an example of another embodiment of a receiving funnel with a tube spout integrated with the receiving funnel.
Figure 23B:
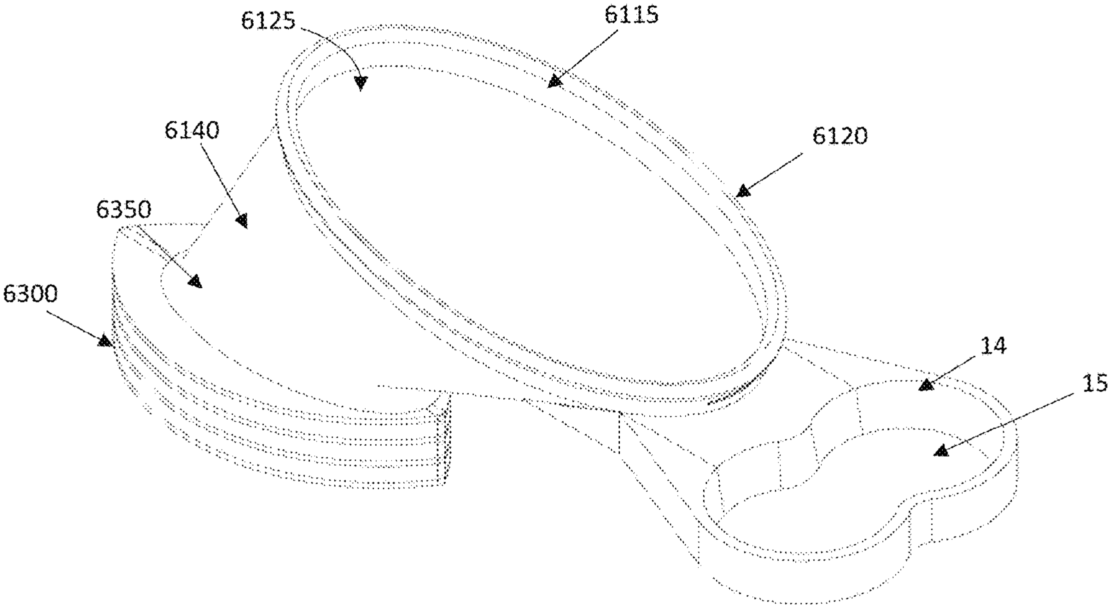
FIG. 23B is a perspective view of the receiving funnel shown in FIG. 23A.
Figure 23C:
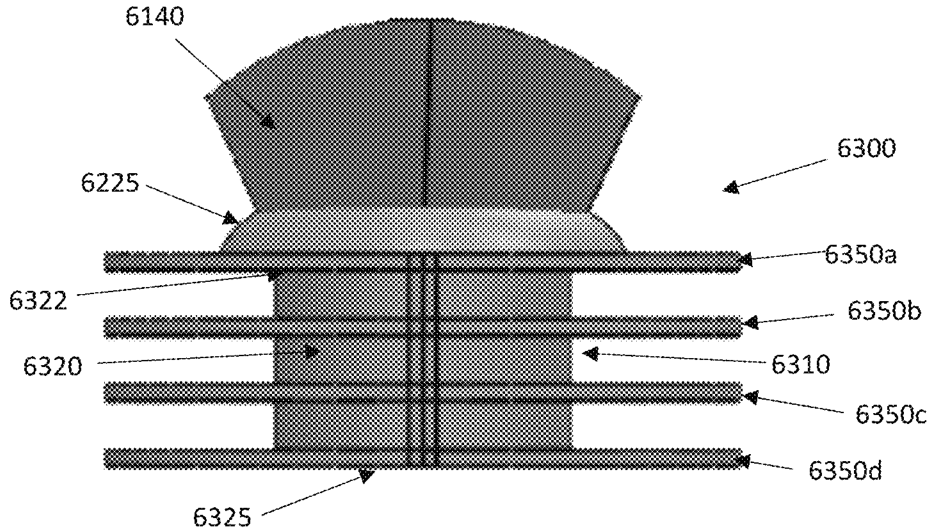
FIG. 23C is a side view of the tube spout of the receiving funnel shown in FIG. 23A.
Figure 23D:
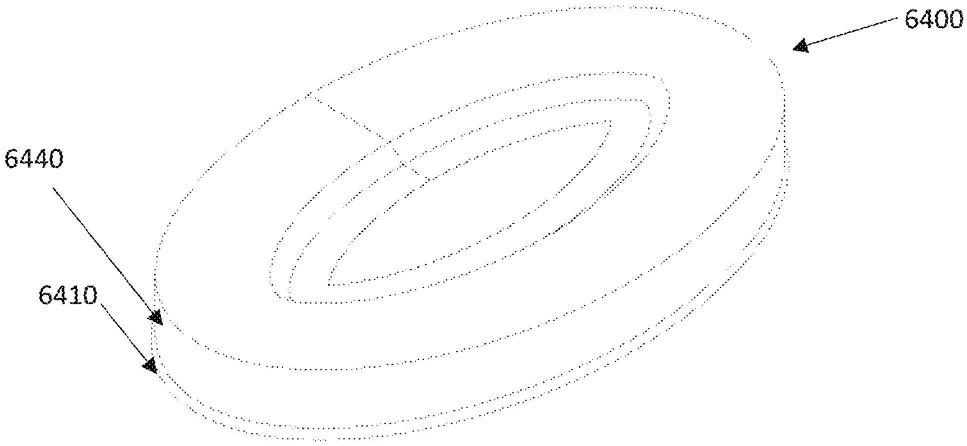
FIG. 23D is a perspective view of a removable lid designed to close an entrance opening of the receiving funnel shown in FIG. 23A.
Figure 23E:
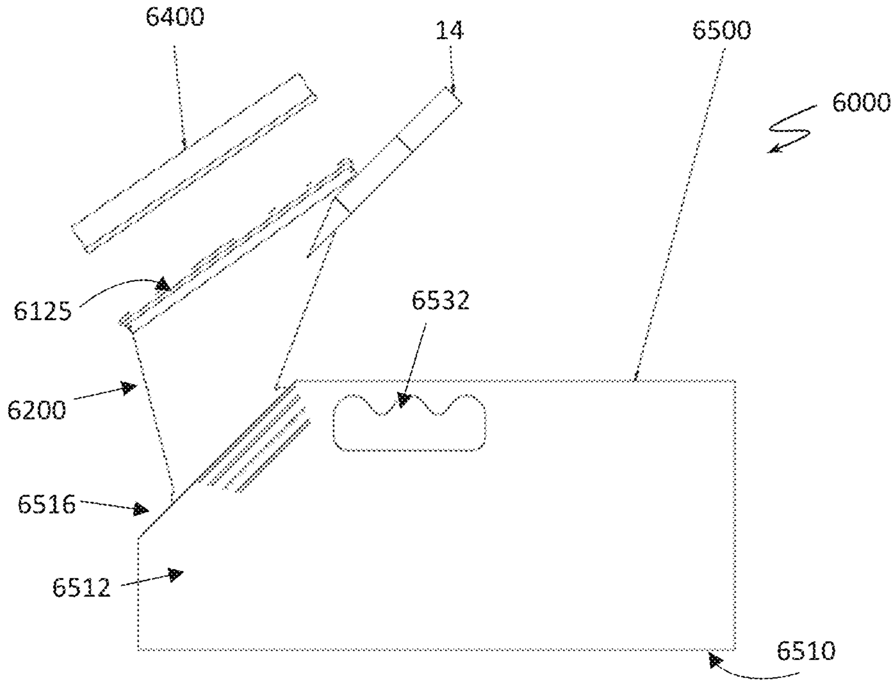
FIG. 23E is a side view of a female urine collection system showing the receiving funnel shown in FIG. 23A with a tube spout sealed to an opening of a collection pouch.
Figure 23F:
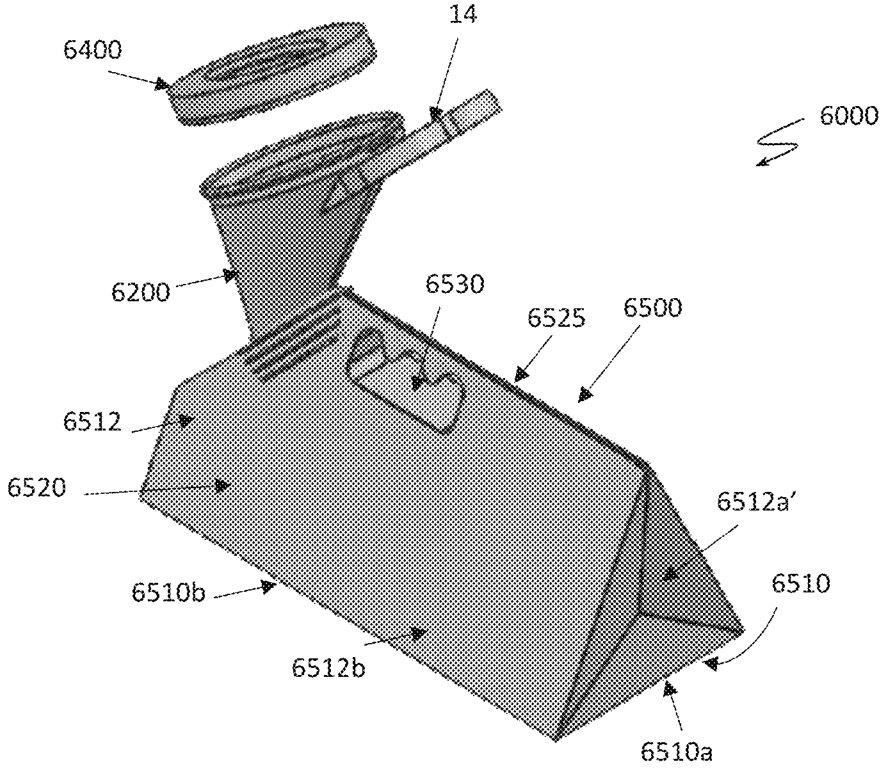
FIG. 23F is a perspective view of the female urine collection system shown in FIG. 23E.

FIGS. 23A-23F show another embodiment of a urine collection system (6000) designed as a spout pouch with a receiving funnel (6200) and a removable lid/cap (6400). FIGS. 23A and 23B show the receiving funnel (6200) with a tube spout (6300) that is integrated to a lower part (6225) of a funnel body (6222). The receiving funnel (6200) has a ring-shaped upper rim (6120) formed at a top edge defining an entrance opening (6125). The upper rim (6120) is similar to the ring-shaped upper rim described herein above with respect to other embodiments of urine collection systems and has rounded corners and sized to fit around user genitalia without causing discomfort or damaging the skin during use. The funnel body (6222) has a side wall (6140) extending downward off the upper rim (6120) to the tube spout (6300). The tube spout (6300) has a body (6310) that defines a passageway (6320) for providing access to an inner cavity of a collection container or pouch (6500). The passageway (6320) of the tube spout (6300) has an upper opening (6322) connected to an exit opening (6260) formed at the lower part (6225) of the receiving funnel (6200) and a lower opening (6325). The tube spout (6300) is sealed to a collecting pouch opening (6550) such that the lower opening (6325) is within the inner cavity of the collection pouch (6500), as shown in FIGS. 23E and 23F.

The tube spout (6300) can further include a number of flanges (6350) that extend radially a predetermined distance from an outer surface of the tube spout body (6310). The flanges (6350) can provide a surface for manipulating the urine collection system (6000) and the collection pouch (6500) during various manufacturing operations, such as for example sealing or the like. In the illustrated example of FIG. 23C, there are four flanges (6350) separated at a predetermined distance one from another. For example, a first flange (6350*a*) can be positioned at a predetermined distance above a second flange (6350*b*), which is at a predetermined distance from a third flange (6350*c*), which is at a predetermined distance from a fourth flange (6350*d*). More or less than four flanges can be provided without departing from the scope of the invention to provide surface to manipulate the collecting pouch and the tube spout during manufacturing and sealing.

The side wall (6140) of the receiving funnel body (6222) can be angled with respect to the tube spout (6300) to allow better positioning and fit of the urine collection system (6000) when in use. The funnel body (6222) can have a concave (cup-like) shape side wall, or straight conical wall, or convex (barrel-like) shape wall as described herein above. A handle (14) with finger opening (15) can be connected to the upper part (6115) of the receiving funnel (6200). The lid or cap (6400), example of which is shown in FIG. 23D, is provided to cover the entrance opening (6125) of the receiving funnel (6200) and serve as a closure to prevent spillage. The lid (6400) can be configured as a snap on type of lid but person skilled in the art would understand that any other type of lid can be used (e.g., push down and turn) without departing from the scope of the invention. The lid (6400) can be designed and sized to tightly fit and engage the outer and inner surface of the funnel side wall (6140) in proximity to the upper rim (6120). The lid (6400) comprises outer collar (6410) that includes an inner wall (6420) and an outer wall (6440), which together define a downwardly open groove (6430) which is configured to grip side wall (6140) when the lid (6400) is disposed over the upper rim (6120), by applying gripping/elastic pressure of the inner wall (6420) and the outer wall (6440) of the lid (6400) against the inner and outer surfaces of the side wall (6140) at the upper part (6115) of the funnel body.

When the urine collection system (6000) is in use the lid (6400) is easily removed and after the use the lid is snapped on to prevent spillage of the collected urine out of the collection system (6000). In one implementation, the tube spout (6300) can comprise an one-way valve formed at the lower opening (6325) to allow urine passing through the lower opening (6325) into the collecting pouch (6500) but prevents collected urine flowing back from the pouch (6500) into the tube spout (6300).

Figure 23G:
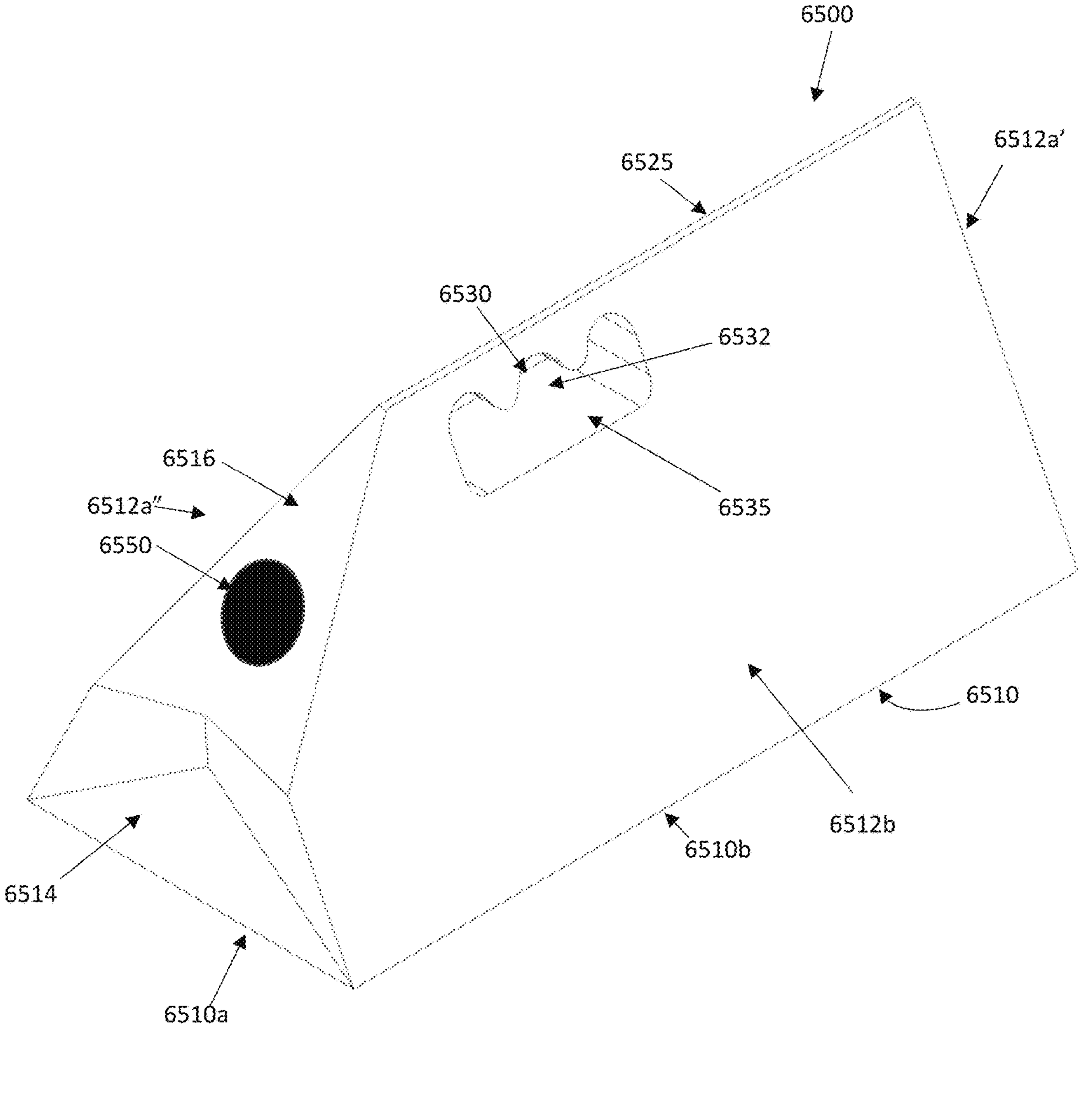
FIG. 23G is a perspective view of the collection pouch shown in FIG. 23E and FIG. 23F.

FIGS. 23E and 23F illustrate the urine collection system (6000) with the collection pouch (6500) tightly connected to the tube spout (6300) of the receiving funnel (6200) and the lid (6400) removed and away from the entrance opening (6125). The collection pouch (6500) can have a flat bottom or base (6510) that allows the collection container (6500) to be self-standing. The base (6510) can have rectangular shape with two long opposite sides and two short opposite sides. The base (6510) is attached to walls (6512) in a tight seal configuration forming the body (6520) of the container (6500) defining the inner cavity of the collecting container (6500). FIG. 23G illustrate in detail the collection pouch (6500) with two narrow side walls (6512*a*) that are connected to the two short sides of the base (6510*a*). One of the narrow side walls (6512*a*') has triangular shape with pleated design and is connected to the base along a lower edge and to the respective long side walls (6512*b*) along respective side edge, such that the pleated side wall (6512*a*') has a height defined by the distance between the base (6510) and the upper edge (6525) of the container (6500). The opposite narrow side wall (6512*a*") has a lower part (6514) that has pleated design and an upper slanted part (6516) that extend from the upper edge of the lower part (6514) to the upper edge (6525) of the collection pouch (6500). The lower part (6514) is connected to the base (6510) along its lower edge and to the respective long side walls (6512*b*) along respective side edges. The upper part (6516) is angled in respect to the lower part (6514) and is connected to the respective long side walls (6512*b*) and its side edges. The two long side walls (6512*b*) that are connected to the long sides (6510*b*) of the base (6510) are connected together along their upper edges forming the upper edge (6525) of the collection pouch (6500). A collection container opening (6550) is formed in the upper part (6516) of the side wall (6512*a*"). The tube spout (6300) is sealed to the opening (6550). The position of the pouch opening (6550) and therefore tube spout (6300) in the illustrated example is in the upper corner of the collection container (6500), however the pouch opening and the tube spout can be positioned at an upper wall (see FIG. 24D) of the collection container without departing from the scope of the invention. At least part of the tube spout (6300) is inserted into the opening (6550) and the collection container is then sealed by heat sealing or ultrasonic seal in a tight seal fashion. The collection container (6500) can further comprise a handle (6530) formed in the upper part of the collecting container (6500) to aid the user to carry the urine collection system (6000). A hand opening (6532) designed and sized to receive human hand is formed in each of the long side walls (6512*b*) and the inner cavity of the collection container (6500) is sealed with additional handle walls (6535). The urine collection system (6000) is configured to be used when the user is in a seated/half-seated position or in a laid down position.

Figure 24A:
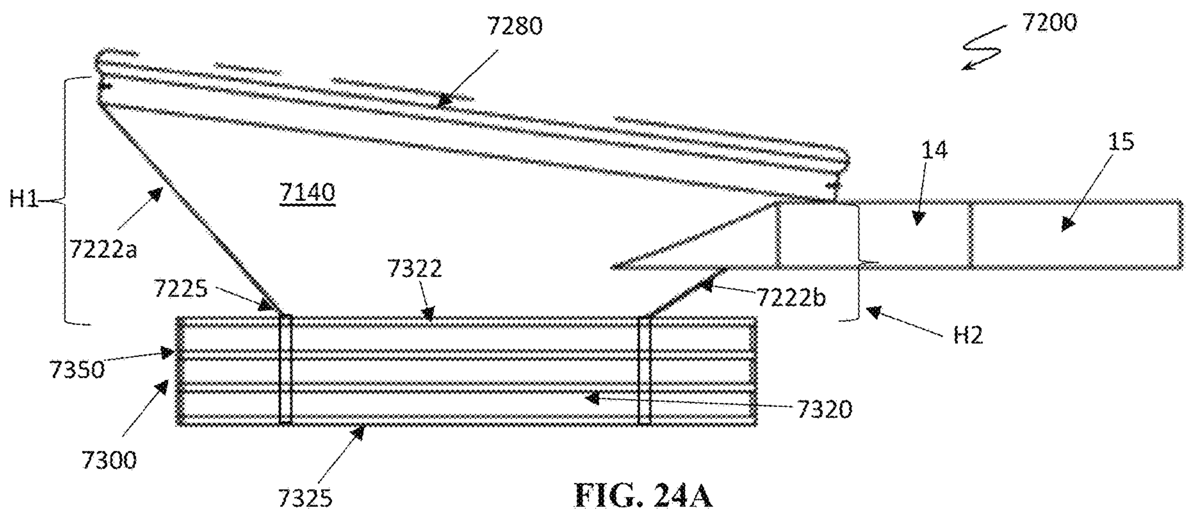
FIG. 24A is a side view of an example of another embodiment of a receiving funnel with a tube spout integrated with the receiving funnel.
Figure 24B:
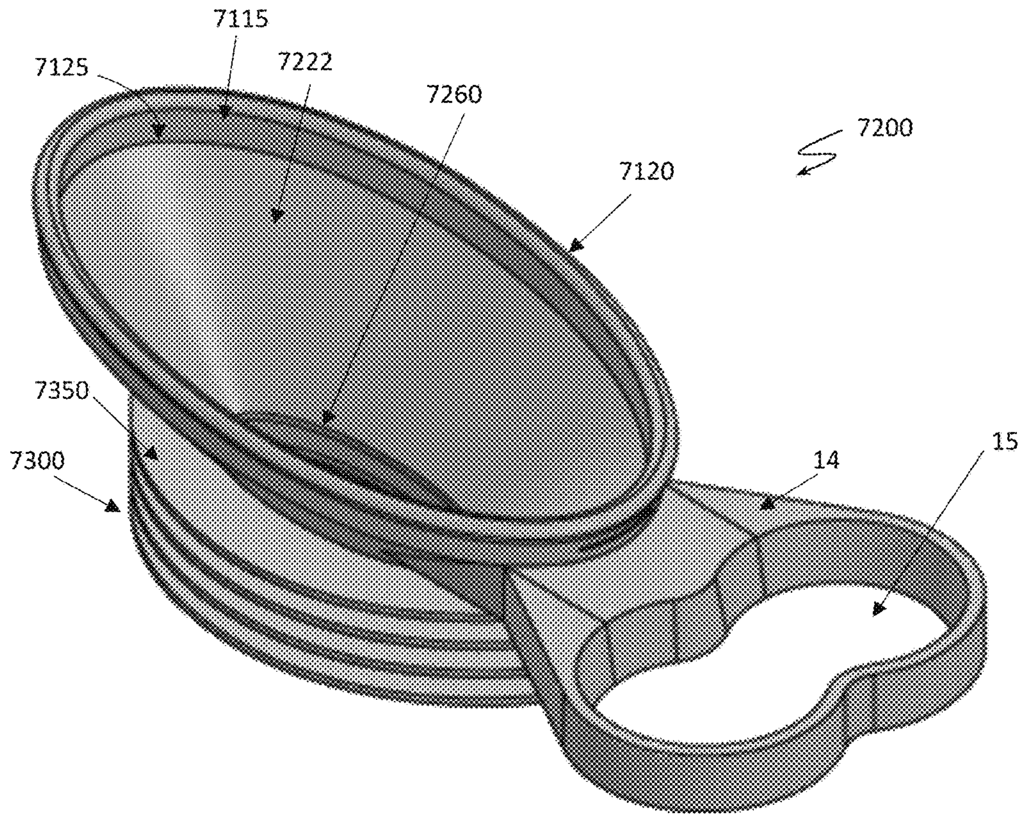
FIG. 24B is a perspective view of the receiving funnel shown in FIG. 24A.
Figure 24C:
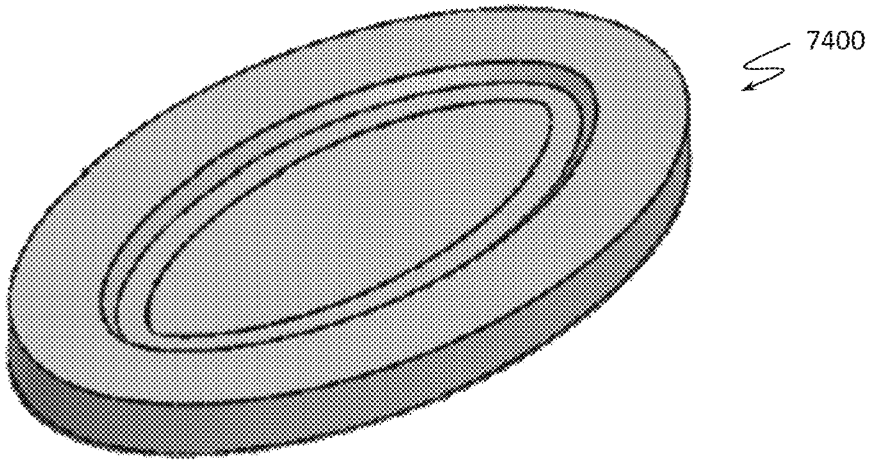
FIG. 24C perspective top view of a removable lid designed to close an entrance opening of the receiving funnel shown in FIG. 24A.
Figure 24D:
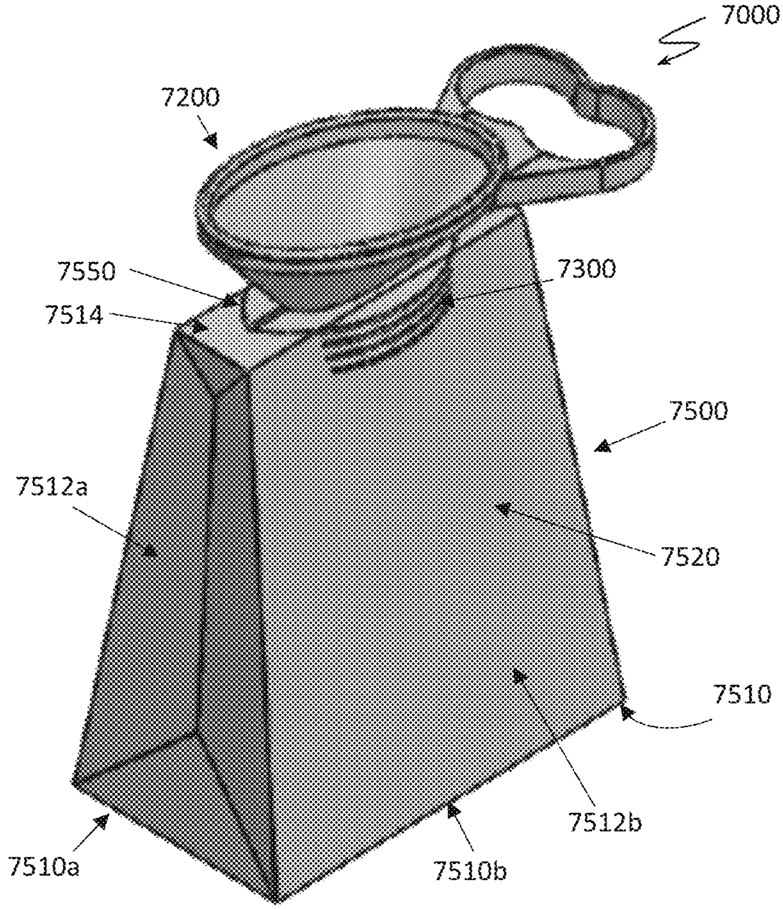
FIG. 24D is a perspective view of a female urine collection system showing the receiving funnel shown in FIG. 24A with a tube spout sealed to an opening of a collection pouch.

FIGS. 24A-24D show another embodiment of a urine collection system (7000), illustrated in FIG. 24D, designed as a spout pouch with a receiving funnel (7200), illustrated in FIGS. 24A and 24B, and a removable lid/cap (7400), illustrated in FIG. 24C. The receiving funnel (7200) includes a tube spout (7300) that is integrated to a lower part (7225) of a funnel body (7222). The receiving funnel (7200) has a ring-shaped upper rim (7120) formed at a top edge defining an entrance opening (7125). The funnel body (7222) has a side wall (7140) extending downward off the upper rim (7125) to the tube spout (7300). The tube spout (7300) is similar to tube spout (6300) of the receiving funnel (6200) described herein above. The tube spout (7300) has a passageway (7320) for providing access to an inner cavity of a collection container or pouch (7500). The passageway (7320) of the tube spout (7300) has an upper opening (7322) connected to an exit opening (7260) formed at the lower part (7225) of the receiving funnel (7200) and a lower opening (7325). The tube spout (9300) is sealed to a collecting pouch opening (7550) such that the lower opening (7325) is within the inner cavity of the collection pouch (7500), as shown in FIG. 24D.

The tube spout (7300) can further include a number of flanges (7350) that extend radially a predetermined distance from an outer surface of the tube spout body. The flanges (7350) similarly to flanges 6350 described herein above with respect to system (6000) can provide a surface for manipulating the urine collection system (7000) and the collection pouch (7500) during various manufacturing operations, such as for example sealing or the like.

The side wall (7140) of the receiving funnel body (7222) can be angled with respect to the tube spout (7300) to allow better positioning and fit of the urine collection system (7000) when in use. Height (H1) at an anterior side (7222*a*) of the receiving funnel body (7222) can be bigger than the height (H2) and the posterior side (7222*b*) of the receiving funnel body (7222), creating therefore upper face (7280) of the receiving funnel (7200) that is slanted to better fit when the system (7000) is in use. The funnel body (7222) can have a concave (cup-like) shape side wall, or straight conical wall, or convex (barrel-like) shape wall as described herein above. A handle (14) with finger opening (15) can be connected to the upper part (7115) of the receiving funnel (7200). The lid or cap (4400), example of which is shown in FIG. 24C, is provided to cover the entrance opening (7125) of the receiving funnel (7200) and serve as a closure to prevent spillage. The lid (7400) can be configured as a snap on type of lid similar to the lid (6400) described herein above. The lid (7400) is designed and sized to tightly fit and engage the outer and inner surface of the funnel side wall (7140) in proximity to the upper rim (7120). When the urine collection system (7000) is in use the lid (7400) is easily removed and after the use the lid is snapped on to prevent spillage of the collected urine out of the collection system (7000).

FIG. 24D illustrate the urine collection system (7000) with the collection pouch (7500) tightly connected to the tube spout (7300) of the receiving funnel (7200). The collection pouch (7500) can have a flat bottom or base (7510) that allows the collection container (7500) to be self-standing. The base (7510) can have rectangular shape with two long opposite sides (7510*b*) and two short opposite sides (7510*a*). The base (7510) is attached to walls (7512) in a tight seal configuration forming the body (7520) of the container (7500) defining the inner cavity of the collecting container (7500). The collection pouch (7500) has two pleated side walls (7512*a*) that are connected to the two short sides of the base (7510*a*) along their respective lower edge and to the respective long side walls (7512*b*) along respective side edges. The two long side walls (7512*b*) are connected to the long sides (7510*b*) of the base (7510) along their respective lower edge. The collection container/pouch (7500) also has an upper wall (7514) that is connected to the two pleated walls (7512*a*) along their respective upper edges and to the two long side walls (7512*b*) along their respective upper edges. A collection container opening (7550) is formed in the upper wall (7514). The tube spout (7300) is sealed to the opening (7550). At least part of the tube spout (7300) is inserted into the opening (7550) and the collection container is then sealed by heat sealing or ultrasonic seal in a tight seal fashion. The urine collection system (7000) is configured to be used when the user is in a standing position.

FIG. 25A shows the recommended ergonomic finger position for the urine collection systems, described herein above, with a handle with single-finger hole design. The user is instructed to place the middle finger into the hole and push with the middle and index fingers to position the upper rim portion against their body during use. The handle is attached to the posterior section of the funnel which can have conical, concave, or convex shape. The user can push the anterior section of the funnel towards the posterior part of the human body at the pubic region such that the genital region is covered by the funnel rim to prevent spillage. FIG. 25B shows the user position when the handle has a double-finger hole design. The user has the middle and ring finders inserted into the hole to hold the handle and push the upper rim against their body with the thumb. FIG. 25C shows the user position when the handle has triple-finger hole design, and the user has the middle, ring, and index fingers inserted into the hole to hold the handle.

Figure 26A:
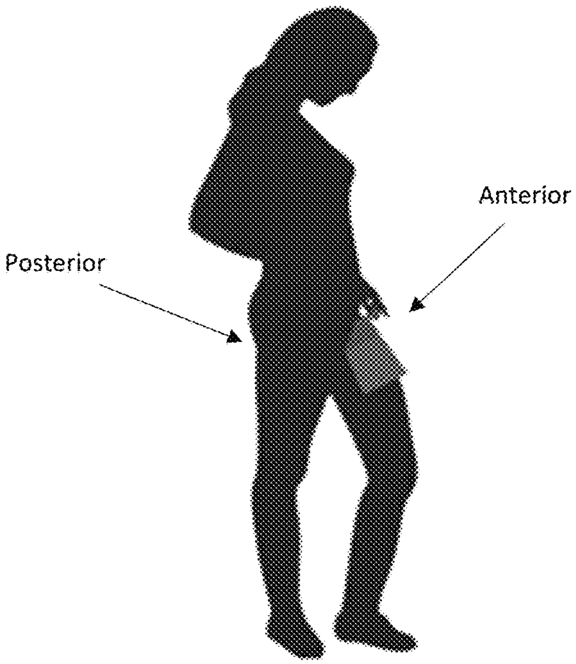
FIGS. 26A-26B is a view of a female urinal collection system when it is positioned against user's genitalia parts during use.
Figure 26B:
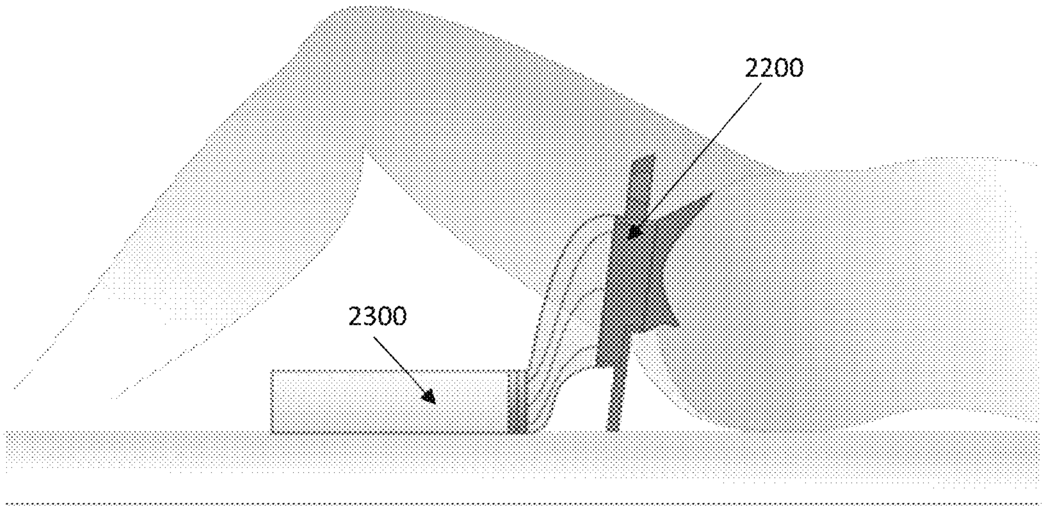

FIG. 26A is a descriptive view illustration of one method of use when a female user is in standing position while FIG. 26B illustrate method of use when the user in in laid down position. The handle is gripped at the front of the user's body, and the rim of the receiving funnel is positioned between the legs such that it hovers below the urethra and covers the pubic region. The ergonomic handle allows the user to grip the funnel at one-end, and to apply pressure to the anterior portion of the vagina, around the labia majore, to act as additional grip and prevent spilling due to increased weight in the collection container. The user, or in some cases the care giver, can position the urine collection device in standing or laying position without having to remove lower-body clothing.

Figure 27:
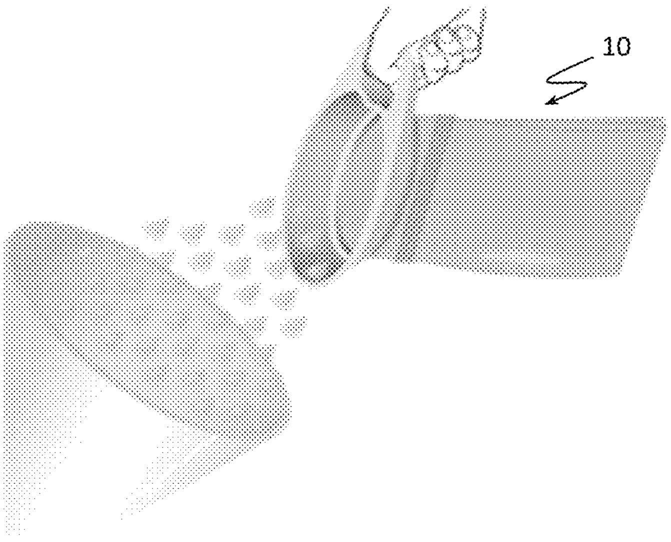
FIG. 27 is showing a urinal collection system of the present invention during emptying urile collected in the urinal collection system into a waterless urinal.
Figure 28:
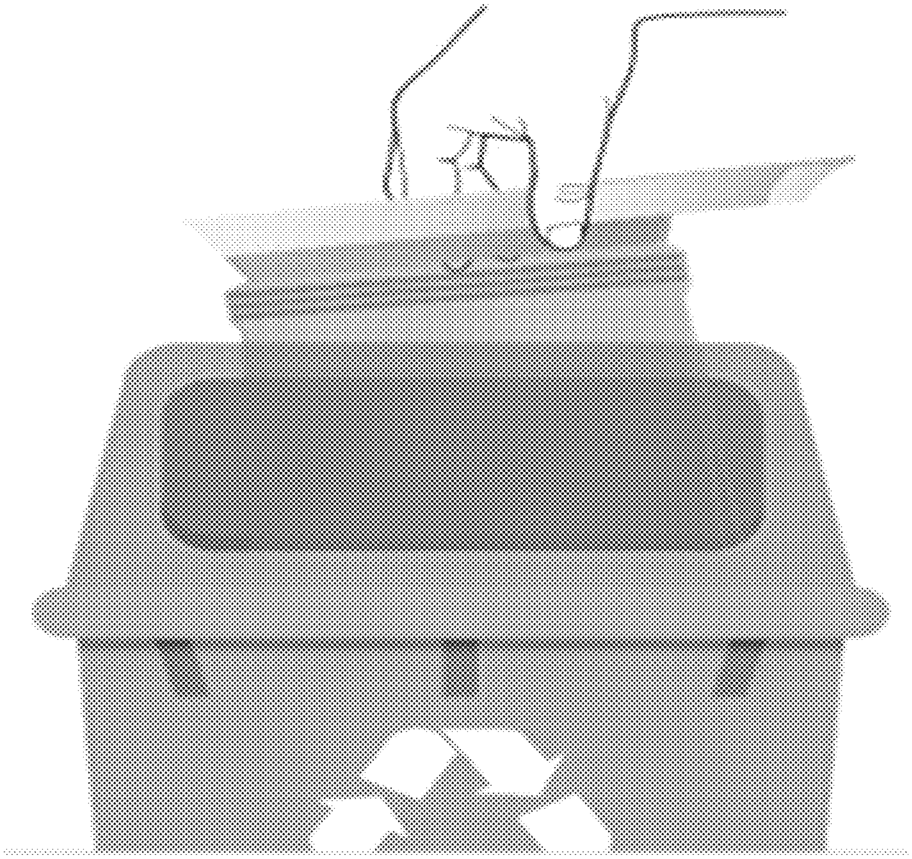
FIG. 28 is showing a dispensable embodiment of a urine collection system after use.

FIG. 27 demonstrates one method for dispensing of the collected urine out of the urine collection unit (10). The collected urine can be dispensed into a waterless urinal or into a low water-flow toilet system by opening the closure to allow the urine to flow out of the container. In addition to the urine collection container and elliptical conic funnel, the dispenser may also comprise of a dispensing mouth and a release element. In one embodiment, a dispensing valve with a release element (not shown) can be provided, such that the urine is dispensed out by turning the release element to open the dispensing valve. This can allow the user to dispense the urine without tilting the container and risking spillage. Once the content in the collection container of the system is emptied, the collection container is collapsed/folded the disposed into recyclable bin as shown in FIG. 28.

Figure 29:
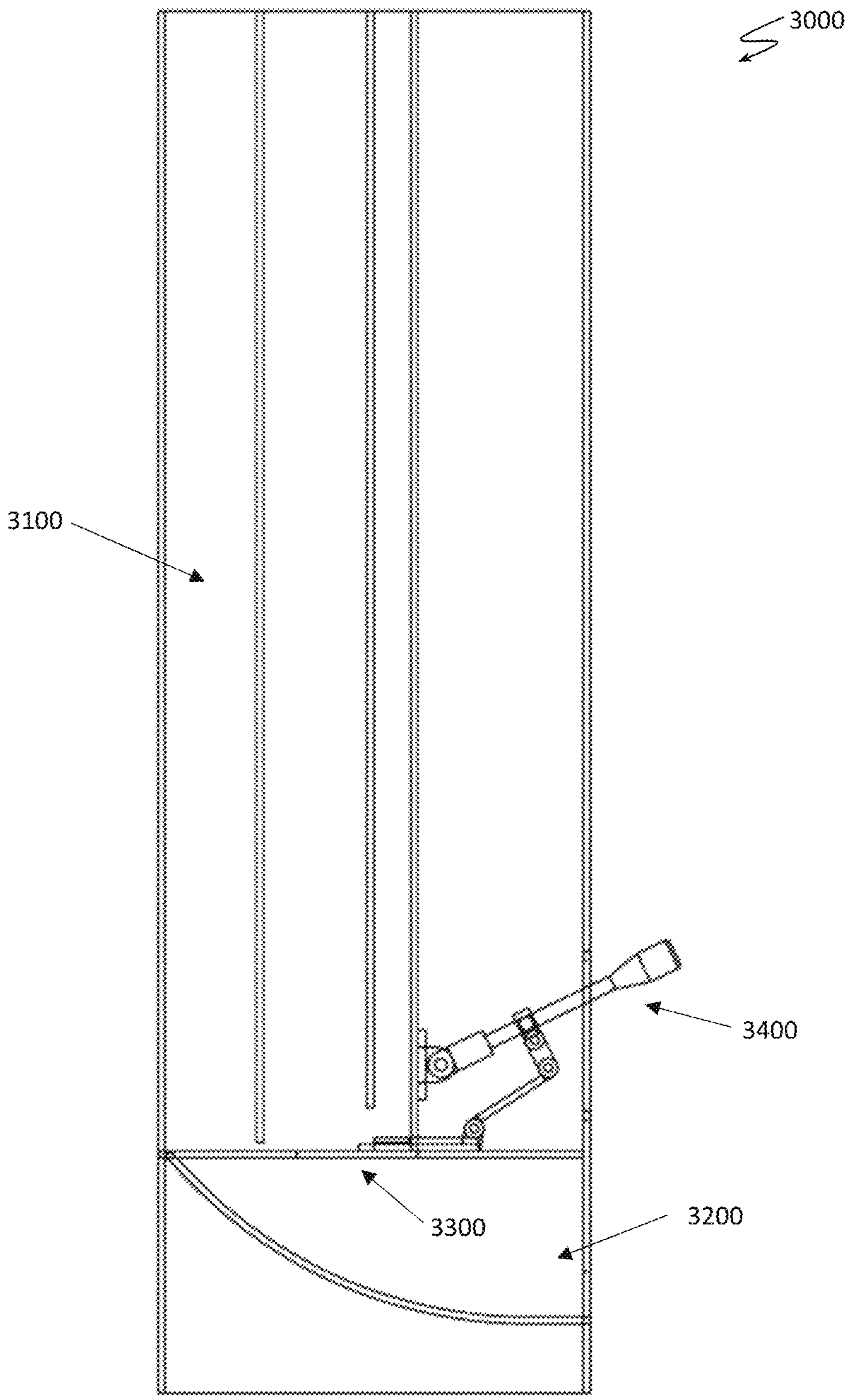
FIG. 29 is a cross-sectional view of an example of a dispenser for dispensing a urine collection system of the present invention.

The urine collection systems can be used in public washrooms to prevent user being exposed to pathogen microorganism by seating on contaminated public seats and to reduce unnecessary water wastage in the public washrooms. FIG. 29 shows a dispenser (3000) that can comprise a number of urine collection systems (10, 100, 1000, 2000, 6000, 7000) as described herein above. The dispenser (3000) can be provided in the public washrooms or medical labs and the user can simply pull out one collection system out of the dispenser for use as described above. The dispenser (3000) can comprise at least one storage container (3100) that contains a plurality of urine collection systems and a dispensing mouth (3200). The urine collection systems when stored in the storage container (3100) are in collapsed position for easier storing and puling them out through the dispensing mouth (3200). In one embodiment, multiple storage containers (3100) can be provided to store collection systems with different volumes. For example, the dispenser can have three storage containers (3100), where first container can store small volume collection systems (10), second storage container can store medium volume collection systems (100) and the third storage container can store large volume collection systems (1000). The dispenser can further comprise a gate (3300) in communication with a gate opener (3400) to open the gate (3300) so that the collection system can be ejected out of the storage container (3100) when the gate (3300) is opened. For example, the gate opener (3400) can be coin operated gate opener design. In some implementation, the dispenser (3000) as described above can be provided in the medical laboratories, so that user can take a collection system of the desire size when they need to provide sample for lab analysis.

While particular elements, embodiments and applications of the present disclosure have been shown and described, it will be understood that the scope of the disclosure is not limited thereto, since modifications can be made by those skilled in the art without departing from the scope of the present disclosure, particularly in light of the foregoing teachings. Thus, for example, in any method or process disclosed herein, the acts or operations making up the method/process may be performed in any suitable sequence and are not necessarily limited to any particular disclosed sequence. Elements and components can be configured or arranged differently, combined, and/or eliminated in various embodiments. The various features and processes described above may be used independently of one another or may be combined in various ways. All possible combinations and sub-combinations are intended to fall within the scope of this disclosure. Reference throughout this disclosure to "some embodiments," "an embodiment," or the like, means that a particular feature, structure, step, process, or characteristic described in connection with the embodiment is included in at least one embodiment. Thus, appearances of the phrases "in some embodiments," "in an embodiment," or the like, throughout this disclosure are not necessarily all referring to the same embodiment and may refer to one or more of the same or different embodiments.

Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Conditional language used herein, such as, among others, "can," "could," "might," "may" "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without operator input or prompting, whether these features, elements and/or steps are included or are to be performed in any particular embodiment. No single feature or group of features is required for or indispensable to any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The example results and parameters of the embodiments described herein are intended to illustrate and not to limit the disclosed embodiments. Other embodiments can be configured and/or operated differently than the illustrative examples described herein.

The invention claimed is:

1. A urine collection system, the system comprising:

a receiving funnel having an upper part and a lower part, the upper part having a ring shape body with an upper rim defining an entrance opening and a side wall extending downwardly from the upper rim, the lower part connected and extending downwardly from a lower edge of the upper part and having a funnel body and an exit opening formed at a bottom edge of the lower part of the receiving funnel, a diameter of the body at the entrance opening is bigger than a diameter of the body at the exit opening, the receiving funnel and the entrance opening sized and shaped to fit around user genitalia parts surrounding a perimetral region of all the genitalia parts;

a handle having a first end connected to the receiving funnel and a second end formed away from the receiving funnel, the handle comprises a hole formed at the second end ergonomically shaped as a multi-fingers hole so that two or more fingers are insertable into the multi-fingers hole during use to position and hold firmly the urine collection system against a user body during use;

a collection container having a body with a base and a side wall extending upward from the base defining a collection cavity and a collection container opening, the opening of the collection container is connected to the lower part of the receiving funnel such that the exit opening of the receiving funnel is in fluid communication with the inner cavity of the collection container, the side wall having two long opposite sides connected to two long sides of the base and two short opposite sides connected to two short sides of the base, one of the short sides comprising a lower part and an upper slanted part extending upwards from an upper edge of the lower part, the collection container opening formed in the upper slanted part of the short side; and a tube spout integrally connected to the lower part of the receiving funnel, the tube spout having a body defining a passageway with an upper opening joined to the exit opening of the receiving funnel and a lower opening the opening of the collecting container is tightly sealed to at least portion of the tube spout such that the lower opening of the tube spout is within the inner cavity of the collection container, wherein the lower part of the of the receiving funnel is angled to the body of the tube spout.

2. The urine collection system of claim 1, wherein the handle is integral and extending outwardly from the upper portion of the receiving funnel.

3. The urine collection system of claim 1, wherein the ring-shape body of the receiving funnel have a straight conical wall.

4. The urine collection system of claim 1, wherein the ring-shape body of the receiving funnel have a concave rounded inwardly wall.

5. The urine collection system of claim 1, wherein the ring-shape body of the receiving funnel have a convex rounded outwardly wall.

6. The urine collection system of claim 1, wherein the system is configured to be used as waterless female urinals.

7. The urine collection system of claim 1, wherein the system is configured to be used as a medical urine samples collection container.

8. The urine collection system of claim 1, wherein the collection container is foldable or collapsible when empty.

9. The urine collection system of claim 8, wherein the collection container has at lease two pleated side walls opposite one to another.

10. The urine collection system of claim 1, wherein the upper part and the lower part of the receiving funnel are detachably connected.

11. The urine collection system of claim 10, further comprising a ledge that extends inwardly of the lower edge of the upper part and a flange that extends outwardly from an upper edge of the lower part of the receiving funnel, when the upper part and the lower part are in an attached position the flange rests on the ledge and the funnel body of the lower part extends downwardly from the lower edge of the upper part.

12. The urine collection system of claim 1, further comprising a removable lid design and sized to close the entrance opening of the receiving funnel.

13. The urine collection system of claim 12, wherein the tube spout further comprises a plurality of flanges that extend radially a predetermined distance from an outer surface of the tube spout body, the flanges being separated at a predetermined distance one from another.

14. The urine collection system of claim 13, wherein and one of the two short opposite sides has pleated design and the lower part of the other of the short sides has a pleated design.

* * * * *